United States Patent

Van Der Wouw et al.

[11] Patent Number: 6,066,356
[45] Date of Patent: May 23, 2000

[54] ARABINOXYLAN DEGRADING ENZYMES

[75] Inventors: Monique Josina Andrea Van Der Wouw, Delft; Albert Johannes Joseph Van Ooijen, Voorburg; Marcus Matheus Catharina Gielkens, Wageningen; Leendert Hendrik De Graaff, Oosterbeek; Jacob Visser, Wageningen, all of Netherlands

[73] Assignee: Gist brocades B.V., Netherlands

[21] Appl. No.: 09/170,354

[22] Filed: Oct. 13, 1998

Related U.S. Application Data

[62] Division of application No. 08/637,763, filed as application No. PCT/EP95/03395, Aug. 28, 1995, Pat. No. 5,849,559.

[30] Foreign Application Priority Data

Aug. 26, 1994 [EP] European Pat. Off. .............. 94202442

[51] Int. Cl.[7] .............................. A23G 1/00; A23G 2/00; C12N 11/00; C12N 9/24; C12N 9/42; C07H 21/04
[52] U.S. Cl. .......................... 426/656; 435/174; 435/200; 435/209; 536/23.2; 426/590
[58] Field of Search .................................... 426/590, 656; 435/174, 200, 209; 536/23.2

[56] References Cited

FOREIGN PATENT DOCUMENTS

| 0 463 706 A1 | 1/1992 | European Pat. Off. . |
| WO 90/01059 | 2/1990 | WIPO . |
| WO 92/19728 | 11/1992 | WIPO . |

OTHER PUBLICATIONS

Conrad, D. et al., "Utilization of Hemicelluloses by Enzymatic Degradation," *Wissenschaft und Umwelt* (1982) 4:242–245 (summary in English).

Gorbacheva, I.V. et al., "Studies on Xylan–Degrading Enzymes—II. Action Pattern of Endo–1,4–β–Xylanase from *Aspergillus niger* Str. 14 0n Xylan and Xylooligosaccharides," *Biochimica et Biophysica Acta*, 484 (1977) 94–102.

Kellett, L.E. et al., "Xylanase B and an arabinofuranosidase from *Pseudomonas fluorescens* subsp. cellulosa contain identical cellulose–binding domains and are encoded by adjacent genes," *Biochem. J.* (1990) 272:369–376.

Kormelink, F.J.M. et al., "Mode of action of the xylan–degrading enzymes from *Aspergillus awamori*," *Xylans and Xyalases*, edited by J. Visser et al. 1992 Elsevier Science Publishers B.V., pp. 141–147.

Kormelink, F.J.M. et al., "Purification and characterization of a (1,4)–β–D–arabinoxylan arabinofuranohydrolase from *Aspergillus awamori*," *Appl Microbiol Biotechnol* (1991) 35:753–758.

*Primary Examiner*—Elizabeth Slobodyansky
*Attorney, Agent, or Firm*—Morrison & Foerster LLP

[57] ABSTRACT

An arabinoxylan-degrading enzyme from Aspergillus is provided. The enzyme is active in the degradation of water-insoluble solids obtained from maize. The enzyme can be used in the preparation of animal feed compositions, human food or in industrial processes.

9 Claims, 5 Drawing Sheets

ARABINOXYLAN DEGRADING ENZYMES

This application is a divisional of application Ser. No. 08/637,763, filed Aug. 5, 1996, now U.S. Pat. No. 5,849,559, which is a 371 of PCT/EP95/03395, filed Aug. 28, 1995.

TECHNICAL FIELD

The present invention relates to the field of molecular biology. In particular, the present invention relates to the cloning and expression of genes encoding polypeptides showing arabinoxylan degrading activity. Thee enzymes are suitably used in industrial processes such as baking of bread, paper and pulp processing and in the preparation of feed and food (additives).

BACKGROUND OF THE INVENTION

The composition of a plant cell wall is complex and variable. Polysaccharides are mainly found in the form of long chains of cellulose (the main structural component of the plant cell wall), hemicellulose (comprising various β-xylan chains) and pectin. The occurrence, distribution and structural features of plant cell wall polysaccharides are determined by (1) plant species; (2) variety; (3) tissue type, (4) growth conditions; (5) ageing and (6) processing of plant material prior to feeding.

Basic differences exist between monocotyledons (e.g. cereals and grasses) and dicotyledons (e.g. clover, rapeseed and soybean) and between the seed and vegetative parts of the plant (Chesson, 1987; Carré and Brillouet, 1986).

Monocotyledons are characterized by the presence of an arabinoxylan complex as the major hemicellulose backbone. The main structure of hemicellulose in dicotyledons is a xyloglucan complex. Moreover, higher pectin concentrations are found in dicotyledons than in monocotyledons. Seeds are generally very high in pectic substances but relatively low in cellulosic material.

Three more or less interacting polysaccharide structures can be distinguished in the cell wall;

(1) the middle lamella forms the exterior cell wall. It also serves as the point of attachment for the individual cells to one another within the plant tissue matrix. The middle lamella consists primarily of calcium salts of highly esterified pectins;

(2) The primary wall is situated just inside the middle lamella. It is a well-organized structure of cellulose microfibrils embedded in an amorphous matrix of pectin, hemicellulose, phenolic esters and proteins;

(3) The secondary wall is formed as the plant matures. During the plant's growth and ageing phase, cellulose microfibrils, hemicellulose and lignin are deposited.

The primary cell wall of mature, metabolically active plant cells (e.g. mesophyll and epidermis) is more susceptible to enzymatic hydrolysis than the secondary cell wall, which by this stage, has become highly lignified.

There is a high degree of interaction between cellulose, hemicellulose and pectin in the cell wall. The enzymatic degradation of these rather intensively cross-linked polysaccharide structures is not a simple process. At least five different enzymes are needed to completely break down an arabinoxylan, for example. The endo-cleavage is effected by the use of an endo-β(1→4)-D-xylanase. Exo-(1→4)-D-xylanase liberates xylose units at the non-reducing end of the polysaccharide. Three other enzymes (α-glucuronidase, α-L-arabinofuranosidase and acetyl esterase) are used to attack substitutents on the xylan backbone. The choice of the specific enzymes is the course dependent on the specific hemicellulose to be degraded (McCleary and Matheson, 1986).

Enzymes that attack side-chains of the xylan backbone can be of interest because they change the characteristics of the polymer, making it more suitable for certain applications. Furthermore these enzymes may act synergistically with main-chain cleaving endo-xylanases (for an extensive review see Kormelink, 1992, PhD thesis, University of Wageningen).

A DNA fragment encoded an arabinoxylan degrading activity is known. In European patent application 463,706, the isolation, characterisation and gene cloning of an endo-xylanase from *Aspergillus tubigensis* is described. This enzyme is not capable of attacking side chains of the arabinoxylan backbone.

Enzymatic activities capable of attacking side chains are also known from *Aspergillus niger* (Kormelink, 1992, supra, Chapters 6 and 7). An enzyme called Arabinofuranosidase A (ArafurA) is characterised by the capacity to release arabinose residues from oligosaccharide structures obtained from arabinoxylans. However, Arafur A is not active on high molecular weight substrates. In addition *Aspergillus niger* produces an enzyme named arafur B which is active on oligosaccharide, as well as high molecular weight arabinoxylan structures. The enzymatic action of ArafurB is confined to releasing arabinose residues from terminal single substituted xylose residues. No DNA fragments are known sofar.

An activity capable of releasing arabinose residues from non-terminal single substituted xylose residues in both oligosaccharide as well as high molecular weight arabinoxylan structures has been isolated from *Aspergillus awamori*. This enzyme is named arabinoxylan arabinofuranose hydrolase (AXH). Sofar no DNA fragments and/or sequence data are available. It is clear that not all enzymes involved in arabinoxylan degradation have been detected yet (Kormelink 1990). For instance, no enzyme attacking xylose molecules double substituted with arabinose, has been found yet. The reason for this is that these enzymes are often secreted in low quantities. Molecular cloning and overproduction in a suitable host of these enzymes, although not easy, its a way to obtain sufficient quantities of pure enzymes, which in turn allows to assess their significance in various applications.

SUMMARY OF THE INVENTION

The present invention provides recombinant DNA comprising a DNA fragment encoding a polypeptide having arabinoxylan degrading activity, or a polypeptide precursor thereof, characterised in that said DNA fragment is selected from:

(a) a DNA fragment encoding a polypeptide having the amino acid sequence represented by amino acids 1 to 306, or a polypeptide precursor of said polypeptide represented by amino acids −27 to 306 in SEQIDNO: 5;

(b) a DNA fragment encoding a polypeptide having the amino acid sequence represented by amino acids 1 to 306, or a precursor of said polypeptide represented by amino acids −27 to 306 in SEQIDNO: 7;

(c) A DNA fragment encoding a variant or portion of the polypeptides represented by amino acid residues 1 to 306 depicted in SEQIDNO: 5 or 7, still having arabinoxylan degrading activity, or a polypeptide precursor thereof;

(d) A DNA fragment coding for a polypeptide having arabinoxylan degrading activity and having the nucleotide sequence represented by nucleotides 784 to 1779 in SEQIDNO: 5 or nucleotides 823 to 1818 in SEQIDNO: 7;

(e) A DNA fragment encoding a polypeptide having arabinoxylan degrading activity, or a part of such polypeptide, which DNA fragment is capable of hybridising to a DNA fragment as represented by nucleotides 784 to 1779 in SEQIDNO: 5 or nucleotides 823 to 1818 in SEQIDNO: 7. The recombinant DNA according to the invention is preferably obtainable from a filamentous fungus, more in particular from an Aspergillus species. Especially preferred recombinant DNA sequences comprise DNA fragments encoding AXDA from *Aspergillus niger* or *tubigensis*.

According to another embodiment, the recombinant DNA according to the invention comprises 5' and 3' regulatory DNA sequences required for the expression of the DNA fragment in a prokaryotic or eukaryotic host cell when present therein. The regulatory DNA sequences are preferably heterologous with respect to the polypeptide coding sequence of said DNA fragment, more preferably said regulatory DNA sequences are selected so as to enhance expression of the DNA fragment in a host compared to expression of the DNA fragment in said host when linked to it homologous regulatory DNA sequences.

According to another embodiment said recombinant DNA is in the form of a vector.

The invention further provides a transformed eukaryotic or prokaryotic host cell comprising recombinant DNA according to their invention, preferably of the genius Aspergillus, as well as a method for obtaining a host cell capable of enhanced expression of an arabinoxylan degrading enzyme by treating a host cell under transforming conditions with a recombinant DNA according to the invention and selecting for the enhanced expression of said arabinoxylan degrading enzyme.

The invention also provides a method for obtaining an arabinoxylan degrading enzyme comprising the steps of growing host cells capable of producing said enzyme under conditions conducive thereto and recovering said enzyme, characterised in that said host cells, or their ancestors, have been transformed with a recombinant DNA according to the invention.

According to yet another embodiment, the invention provides a substantially pure polypeptide having arabinoxylan degrading activity and which is characterised by the amino acid sequence depicted in SEQIDNO: 6 or SEQIDNO: 8, as well as genetic variants and portions thereof still having the said activity. The invention also envisions a composition comprising a substantially pure polypeptide according to claim 1 formulated for use in feed, food, or paper and pulp processing, optionally wherein the enzyme is immobilised.

Also provided are methods of use of a polypeptide according to the invention to assist in arabinoxylan degradation, as a feed or food additive, in paper and pulp processing and baking bread.

Also claimed are a feed or food containing a polypeptide according to the invention.

According to yet another embodiment recombinant DNA is provided, comprising a DNA fragment represented by nucleotides 1 to 783 of SEQIDNO: 5, or a subfragment thereof, capable of regulating expression of a DNA sequence attached to it, as well as recombinant DNA comprising a DNA fragment represented by nucleotides 1 to 822 of SEQIDNO: 7, or a subfragment thereof, capable of regulating expression of a DNA sequence attached to it.

The invention is further illustrated by the description of the following figures.

DETAILED DESCRIPTION OF THE INVENTION

Figure 1:
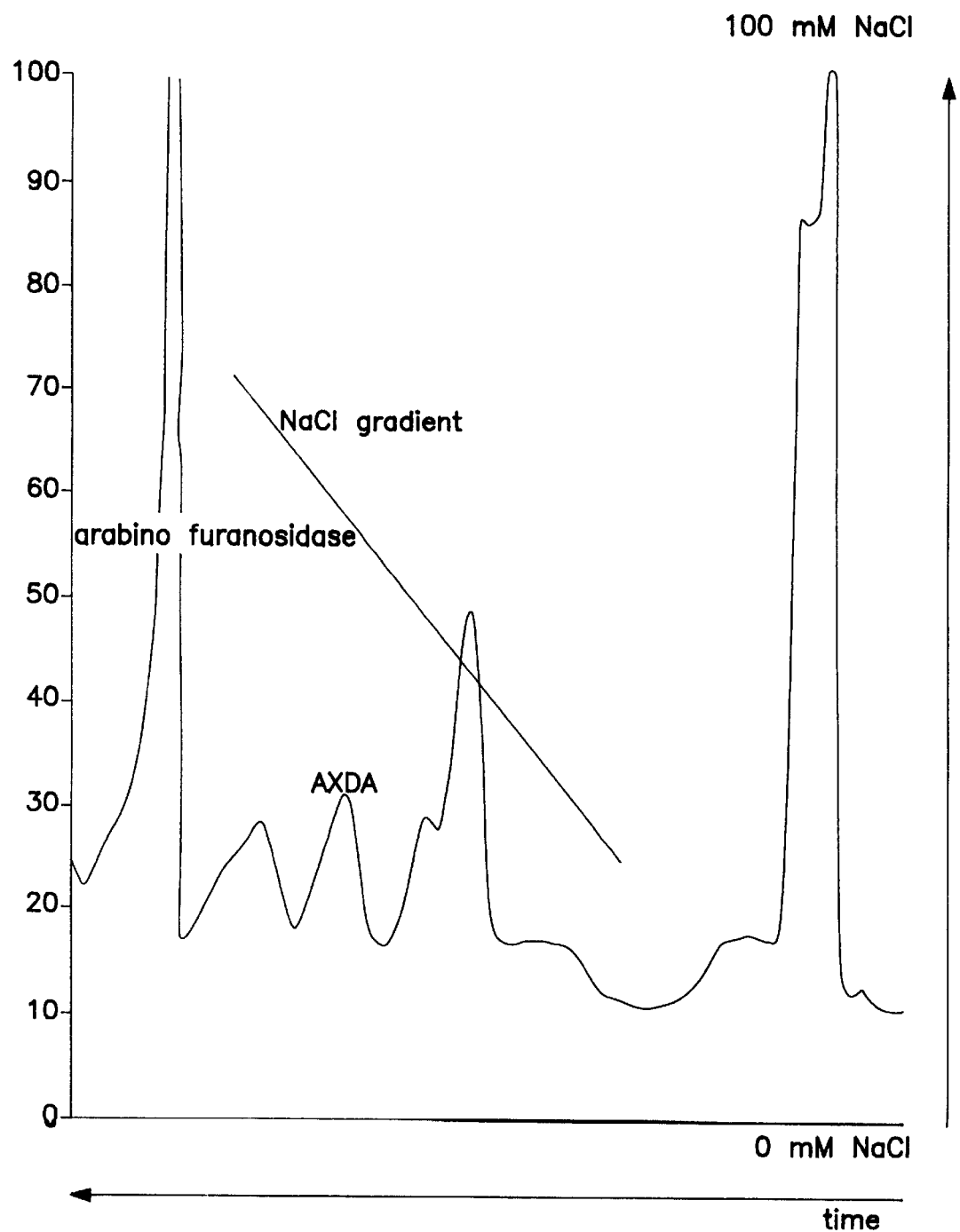
FIG. 1 elution profile (OD280) of arabinoxylan degrading activity on HPLC.

The present invention provides purified and isolated DNA molecules comprising the sequence of arabinoxylan degrading enzyme genes and genetic variants thereof. The DNA molecules may include the arabinoxylan degrading enzyme encoding region as well as their adjacent 5' and 3' regulatory regions. Genetic variants include DNA molecules encoding mutant arabinoxylan proteins and degenerated DNA molecules wherein the desired activity of the enzyme expressed therefrom is retained.

The present invention also provides DNA constructs for the expression of arabinoxylan degrading enzymes in a desired expression host. These expression constructs include hybird DNA molecules containing the arabinoxylan degrading enzymes encoding regions operably linked to regulatory regions, such as promoter, secretion and terminator signals originating from homologous or heterologous organisms, these regulatory regions being capable of directing the enhanced expression of the enzyme encoded by the arabinoxylan degrading enzyme encoding DNA molecule in an appropriate host. Preferably, the expression construct will be integrated into the genome of the selected expression host. The present invention further provides vectors, preferably plasmids, for the cloning and/or transformation of microbial hosts via the introduction into the microbial host of the DNA constructs for the expression of the arabinoxylan degrading enzymes.

In addition, the present invention provides homologous or heterologous hosts transformed with vectors containing the DNA constructs described above. Heterologous hosts may be selected from bacteria, yeasts or fungi.

Within the context of the present invention, the term "homologous" is understood to intend all that which is native to the DNA molecule encoding the arabinoxylan degrading enzyme of interest, including its regulatory regions. A homologous host is defined as the species from which such DNA molecules may be isolated.

The term "heterologous" is thus defined as all that which is not native to the DNA molecule encoding the arabinoxylan degrading enzyme of interest itself, including regulatory regions. A "heterologous" host is defined as any microbial species other than that from which the arabinoxylan degrading enzyme encoding genes have been isolated.

Within the context of the present invention, the phrase "enhanced expression of the arabinoxylan degrading enzyme of interest" is defined as the expression of the arabinoxylan degrading enzyme of interest at levels above that which are ordinarily encountered in the homologous wild-type organism. In the same context, enhanced expression also intends the expression of the arabinoxylan degrading enzymes of interest in a heterologous organism which does not normally produce such arabinoxylan degrading enzymes except for the introduction of the DNA molecule or expression construct encoding the arabinoxylan degrading enzymes of interest into the heterologous expression host. Progeny of these expression hosts are, of course, also to be understood to be embraced by the present invention.

The present invention also includes DNA sequences which hybridize to the DNA sequences obtainable from the fungi described above, but which may differ in codon sequence due to the degeneracy of the genetic code or cross-species variation. Thus, the invention includes DNA fragments coding for arabinoxylan degrading enzymes obtainable from other species than Aspergillus. Typically, procedures to obtain similar DNA fragments involve the screening of bacteria or bacteriophage plaques transformed with recombinant plasmids containing DNA fragments from an organism known or expected to produce an arabinoxylan degrading enzyme according to the invention. After in situ replication of the DNA, the DNA is released from the cells or plaques, and immobilised onto filters (generally nitrocellulose). The filters may then be screened for complementary DNA fragments using a labelled nucleic acid probe based on any of the sequences determined for the Aspergillus axdA genes. Dependent on whether or not the organism to be screened for is distantly or closely related, the hybridisation and washing conditions should be adapted in order to pick up true positives and reduce the amount of false positives. A typical procedure for the hybridisation of filter-immobilised DNA is described in Chapter 5, Table 3, pp. 120 and 121 in: Nucleic acid hybridisation—a practical approach, B. D. Hames & S. J. Higgins Eds., 1985, IRL Press, Oxford). Although the optimal conditions are usually determined empirically, a few useful rules of thumb can be given for closely and less closely related sequence.

In order to identify DNA fragments very closely related to the probe, the hybridisation is performed as described in Table 3 of Hames & Higgins, supra, (the essentials of which are reproduced below) with a final washing step at high stringency in 0.1*SET buffer (20 times SET=3 M NaCl, 20 mM EDTA, 0.4 M Tris-HCl, Ph 7.8), 0.1% SDS) at 68° Celsius.

To identify sequences with limited homology to the probe the procedure to be followed is as the Table 3 of Hames & Higgins, supra, but with reduced temperature of hybridisation and washing. A final wash at 2*SET buffer, 50° C. for example should allow the identification of sequences having about 75% homology. As is well known to the person having ordinary skill in the art, the exact relationship between homology and hybridisation conditions depend on the length of the probe, the base composition (% of G+C) and the distribution of the mismatches; a random distribution has a stronger decreasing effect on $T_m$ then a non-random or clustered pattern of mismatches.

The above conditions apply for probes having a length of at least 300 bp, preferably at least 500 bp, more preferably about 1 kbp, and a GC-content of the DNA to be probed of about 50±10%. If the GC-content of a given organism is known, then the conditions may be optimised empirically taking into account the following equation (at 1 M, NaCl, within the range 35%≦(% G+C)≦75%): $T_m$=81.5° C.+0.41*(% G+C). Roughly, this means that if the GC-content (% G+C) is 10% higher than average, (stringent) hybridisation conditions may be adjusted by increasing the hybridisation and washing temperature with about 4° C.

For the purposes of this disclosure, a DNA fragment which is said to hybridise to the DNA fragment according to the invention, is defined as giving a positive signal on immobilised DNA after hybridisation with a probe of at least 300 bp, preferably 500 bp, more preferably 1 kbp of any of the sequences depicted in SEQIDNO: 5 or 7, and washing following the procedure of Table 3 in Chapter 5 of Hames & Higgins (as reproduced in essence below) at a temperature of 50° C., 2*SET buffer (i.e. 0.3 M NaCl).

The essential of the procedure described in Table 3, Chapter 5 of Hames & Higgins are as follows:

(1) prehybridisation of the filters in the absence of probe, (2) hybridisation at a temperature between 50 and 68° C. in between 0.1 and 4*SET buffer (depending on the stringency), 10*Denhardt's solution (100*Denhardt's solution contains 2% bovine serum albumin, 2% Ficoll, 2% polvinylpyrrolidone), 0.1% SDS, 0.1% sodiumpyrophosphate, 50 µg/ml salmon sperm DNA (from a stock obtainable by dissolving 1 mg/ml of salmon sperm DNA, sonicated to a length of 200 to 500 bp, allowed to stand in a water bath for 20 min., and diluted with water to a final concentration of 1 mg/ml); hybridisation time is not too critical and may be anywhere between 1 and 24 hours, preferably about 16 hours (o/n); the probe is typically labelled by nick-translation using $^{32}P$ as radioactive label to a specific activity of between $5*10^7$ and $5*10^8$ c.p.m./µg;

(3) (repeated) washing of the filter with 3*SET, 0.1% SDS, 0.1% sodiumpyrophosphate at 68° C. at a temperature between 50° C. and 68° C. (dependent on the stringency desired), repeated washing while lowering the SET concentration to 0.1%., washing once for 0 min. in 4*SET at room temperature, drying filters on 3 MM paper, exposure of filters to X-ray film in a cassette at −70° C. for between 1 hour and 96 hours (depending on the strength of the signal), and developing the film.

Generally, volumina of the prehybridisation and hybridisation mixes should be kept at a minimum. All "wet" steps may be carried out in little sealed bags in a pre-heated water bath.

The above procedure serves to define the DNA fragments said to hybridise according to the invention. Obviously, numerous modifications may be made to the procedure to identify and isolate DNA fragments according to the invention. It is to be understood, that the DNA fragments so obtained fall under the terms of the claims whenever they can be detected following the above procedure, irrespective of whether they have actually been identified and/or isolated using this procedure.

Numerous protocols, which can suitably be used to identify and isolate DNA fragments according to the invention, have been described in the literature and in handbooks, including the quoted Hames & Higgins, supra).

The above procedure is for polynucleotide probes. When oligonucleotide probes are being used the relationship between the $T_d$, the temperature at which a perfectly matching hybrid is half-dissociated, is estimated by the relationship: $T_d$=4° C. per GC base pair +2° C. per AT base pair. On the basis of existing protocols and using this rule of thumb, also oligonucleotide probes may be designed to effectively isolate DNA fragments encoding arabinoxylan degrading enzymes according to the invention from related and more distant organisms. The procedure using oligonucleotides is particularly useful if an enzyme has been purified from a different source and part of the amino acid sequence has been determined. Using this sequence a set of degenerate probes can be made for the screening of a DNA library or Southern blot, essentially as described above.

Good candidates for screening are other filamentous fungi, such as Trichoderma, Penicillium, Dichotomitus squalus, Disporotrichum dimophosporum, and bacteria, such as Bacillus species, and the like. If the initial screening results in clones which appear to contain hybridising fragments, such fragments may be isolated and, if desirable sequenced to determine sequence similarities.

Once an arabinoxylan degrading enzyme of interest has been identified, the DNA sequence encoding such an enzyme may be obtained from the filamentous fungus which naturally produces it by culturing the fungus in an arabinoxylan-containing medium, isolating the desired arabinoxylan degrading enzyme using known methods such as those outlined in Example 1 and determining at least a portion of the amino acid sequence of the purified protein.

DNA probes may thereafter be obtained by designing oligonucleotide sequences based on the deduced partial amino acid sequence. Amino acid sequences may be determined from the N-terminus of the complete protein and/or from the N-termini of internal peptide fragments obtained via proteolytic or chemical digestion of the complete protein. Once obtained, the DNA probe(s) are then used to screen a genomic or cDNA library.

A genomic library may be prepared by partially digesting the fungal chromosomal DNA with a restriction enzyme which recognizes a DNA sequence of four successive nucleotides, e.g. Sau3A, and cloning the resulting fragments in a suitable plasmid or lambda phage vector, e.g. lambda GEM-11.

Alternatively, a cDNA library may be prepared by cloning cDNA, synthesized from mRNA isolated from fungal cells induced for the synthesis of an arabinoxylan degrading enzyme, into an appropriate phage vector, e.g. lambda gt 10.

Subsequently, after plating of a sufficient amount of colonies or plaques, the genomic or cDNA library may be screened with a suitable DNA probe.

If this method is unsuccessful, the genomic or cDNA library may be differentially screened with cDNA probes obtained from mRNA from non-induced and induced cells. Induces mRNA is prepared from cells grown on media containing arabinoxylan as a carbon source, while non-induced mRNA must be isolated from cells grown on a carbon source other than arabinoxylan, e.g. glucose. Among the clones which only hybridize with the induced cDNA probe, a clone containing the desired arabinoxylan degrading enzyme encoding gene may be recovered. Alternatively, an arabinoxylan degrading enzyme gene may be identified by cross-hybridization with a related sequence.

Preferably, oligonucleotide probes are obtained from the N-terminal amino acid sequence (see Example 1.5.1) of an arabinoxylan degrading enzyme having an apparent molecular weight of 32 kDa purified from an *Aspergillus niger* culture filtrate and/or form the amino acid sequence of an internal peptide fragment (see Example 1.5.2) obtained by digestion of the enzyme with CNBr.

The oligonucleotide mixtures are developed can be used to hybridize with both genomic and cDNA libraries. Alternatively and as illustrated herein. The purified AXDA enzyme is used to raise antibodies. The antibodies are use in the immunoscreening of expression libraries. Thus AXDA expression clones are identified. It should be noted that the protein is isolated from *A. niger* var *tubigensis* and the cDNA is isolated from *A. niger* N400 illustrating that different Aspergilli contain AXDA activity.

With the advent of new DNA amplification techniques, such as direct or inverted PCR, it is also possible to clone DNA fragments in vitro once terminal sequences of the coding region are known.

The availability of a DNA sequence encoding an arabinoxylan degrading enzyme enables the construction of mutant enzyme molecules by site-directed mutagenesis. If the tertiary structure of the arabinoxylan degrading enzyme is known, and its catalytic and substrate binding domains are localized, amino acids may be selected for mutagenesis (for example with the aid of computer modelling) which most likely affect catalytic and/or substrate binding functions. If the tertiary structure of the protein is not available, random mutants may be either generated along with the entire coding sequence, or the tertiary structure of the protein may be predicted by comparison with similar known enzymes isolated from another microorganism.

to facilitate the insertion of the DNA fragment containing the AXDA encoding sequence into expression constructs comprising one or more heterologous regulatory regions, the polymerase chain reaction (PCR) (PCR Technology: Principles and Applications for DNA Amplification, (1989) H. A. Ehrlich, ed., Stockton Press, New York) may be used for introduction of appropriate restriction enzyme sites in the 5' and 3' ends of the AXDA coding sequence. The choice of restriction sites depends on the DNA sequence of the expression vector, i.e. the presence of other restriction sites within the DNA molecule.

To obtain the enhance expression of the AXDA proteins in the original (homologous) production species, or alternatively in a heterologous fungal strain, the AXDA encoding DNA regions, including their own control region, are introduced into the selected expression host to increase the copy number of the gene and, consequently, protein expression.

If a heterologous expression host is preferred, and a yeast or a bacterial strain is selected, an uninterrupted (introless) DNA molecule is used for the construction of a heterologous expression vector in order to avoid the possibility that splice signals residing on the genomic fragment are not recognized by the heterologous host. This uninterrupted DNA molecule may be obtained from a cDNA library constructed from mRNA isolated from cells, induced for the synthesis of AXDA. This library may be screened with an oligonucleotide or cDNA probe obtained as described before. Alternatively, an uninterrupted DNA molecule may be obtained by applying a polymerase chain reaction using appropriate 5' and 3' oligonucleotides on their first strand cDNA synthesized from the RNA of arabinoxylan-induced cells.

Enhanced expression of the AXDA of interest may also be achieved by the selection of heterologous regulatory regions, e.g promoter, secretion leader and terminator regions, which serve to increase expression and, if desired, secretion levels of the protein of interest from the chosen expression host and/or to provide for the inducible control of the expression of the AXDA of interest.

Aside from the AXDA of interest's native promoter, other promoters may be used to direct its expression. The promoter may be selected for its efficiency in directing the expression of the AXDA of interest in the desired expression host.

In another embodiment, a constitutive promoter may be selected to direct the expression of the desired AXDA, relatively free from other enzymes. Such as expression construct is furthermore advantageous since it circumvents the need to culture the expression hosts on a medium containing arabinoxylans as an inducing substrate.

Examples of strong constitutive and/or inducible promoters which are preferred for use in fungal expression hosts are the ATP-synthetase, subunit 9 (oliC), triose phosphate isomerase (tpi), alcohol dehydrogenase (adhA), α-amylase (amy), glucoamylase (gam), acetamidase (amdS) and glyceraldehyde-3-phosphate dehydrogenase (gpd) promoters.

Examples of strong yeast promoters are the alcohol dehydrogenase, lactase, 3-phosphoglycerate kinase and triosephosphate isomerase promoters.

Examples of strong bacterial promoters are the α-amylase and Spo2 promoters as well as promoters from extracellular protease genes.

Hybird promoters may also advantageously be used to improve inducible regulation of the expression construct.

Often, it is desirable for the AXDA of interest to be secreted from the expression host into the culture medium.

According to the present invention, the AXDA of interest's native secretion leader sequence may be used to effect the secretion of the expressed AXDA.

However, an increase in the expression of the enzyme sometimes results in the production of the protein in levels beyond that which the expression host is capable of processing and secreting, creating a bottleneck such that the protein product accumulates within the cell. Accordingly, the present invention also provides heterologous leader sequences to provide for the most efficient secretion of the enzyme from the chose expression host.

According to the present invention, the secretion leader may be selected on the basis of the desired expression host. A heterologous secretion leader may be chosen which is homologous to the other regulatory regions of the expression construct. For example, the leader of the highly secreted glucoamylase protein may be used in combination with the glucoamylase promoter itself, as well as in combination with other promoters. Hybrid signal sequences may also advantageously be used within the context of the present invention.

Examples of preferred heterologous secretion leader sequences are those originating from the glucoamylase gene (fungi), the α-factor gene (yeasts) or the α-amylase gene (Bacillus).

In general, terminators are not considered to be critical elements for the enhanced expression of genes. If desired, a terminator may be selected from the same genes as the promoters, or alternatively, the homologous terminator may be employed.

In addition to the genomic fragment mentioned above, the transforming DNA may contain a selection marker to discriminate cells which have incorporated the desired gene from the bulk of untransformed cells. This selection marker, provided with the appropriate 5' and 3' regulatory sequences, may reside on the same DNA molecule containing the desired gene or be present on a separate molecule. In the latter case, a co-transformation must be performed. The ratio of the expression vector/selection vector must be adjusted in such a manner that a high percentage of the selected transformants also have incorporated the vector containing the expression construct of the AXDA of interest.

The most suitable selection systems for industrial microorganisms are those formed by the group of selection markers which do not require a mutation in the host organism. Examples of fungal selection markers are the genes for acetamidase (amdS), ATP synthetase, subunit 9 (oliC) and benomyl resistance (benA). Exemplary of non-fungal selection markers are the bacterial G418 resistance gene (this may also be used in yeast, but not in fungi), the ampicillin resistance gene (*E. coli*) and the neomycin resistance gene (Bacillus).

Once the desired expression construct has been assembled, it is transformed into a suitable cloning host such as *E. coli* to propagate the construct. Afterwards, the expression construct is introduced into a suitable expression host wherein the expression construct is preferably integrated into the genome. Certain hosts such as Bacillus species may be used as both cloning and expression hosts, thus avoiding an extra transformation step.

According to the present invention, a variety of organisms may be used as hosts for the production of the AXDA of interest.

In one embodiment, a homologous expression host may be used. This involves the introduction of the expression construct back into the strain from which the AXDA encoding DNA sequence was isolated either in increased gene copy numbers, or under the control of heterologous regulatory regions as described above, or both.

In another embodiment, an AXDA of interest may be produced by introducing and expression the DNA construct encoding the arabinoxylan degrading enzyme of interest under the control of the appropriate regulatory regions in heterologous hosts such as bacteria, yeasts or fungi. For that purpose, the DNA sequences encoding the AXDA of interest is preferably expressed under the control of promoter and terminator sequences originating from the heterologous host. In addition, it may be necessary to replace the native secretion leader sequence with a leader sequence homologous to the expression host in order to achieve the most efficient expression and secretion of the product.

Factors such as the size (molecular weight), the need for proper glycosylation or the desirability of the extracellular secretion of the AXDA of interest play an important role in the selection of the expression host.

The gram-negative bacterium *E. coli* is widely used as a host for heterologous gene expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus Bacillus are very suitable as heterologous hosts because of their capability to secrete proteins into the culture medium.

Depending on the nature of the AXDA encoding DNA molecule itself, and/or the desirability for further processing of the expressed protein, eukaryotic hosts such as yeasts or fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a fungal host organism should be selected.

A heterologous host may also be chosen to express the AXDA of interest substantially free from other polysaccharide-degrading enzymes by choosing a host which does not normally produce such enzymes such as *Kluyveromyces lactis*.

Examples of preferred expression hosts within the scope of the present invention are fungi such as Aspergillus species (described in EP 184.438 and EP 284.603) and Trichoderma species, bacteria such as Bacillus species (described in EP 134.048) and yeasts such as Kluyveromyces species (described in EP 96.340 and EP 301.670) and Saccharomyces species.

Particularly preferred expression hosts may be selected from *Aspergillus niger, Aspergillus niger* var. *awamori,*

*Aspergillus aculeatis, Aspergillus oryzae, Trichoderma reesei, Bacillus subtilis, Bacillus licheniformis, Baccillus amyloliquefaciens, Kluyveromyces lactis* and *Saccharomyces cerevisiae*.

The expression of the AXDA enzyme of interest is effected by the culturing of the expression hosts, which have been transformed with the appropriate expression construct, in a conventional nutrient fermentation medium.

The fermentation medium consists of an ordinary culture medium containing a carbon source (e.g. glucose, maltose, molasses, etc.), a nitrogen source (e.g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.). Optionally, an inducer (arabinoxylan) may be included.

The selection of the appropriate medium may be based on the choice of expression hosts and/or based on the regulatory requirements of the expression construct. Such media are well-known to those skilled in the art. The medium may, if desired, contain additional components favouring the transformed expression hosts over other potentially contaminating microorganisms.

The fermentation is performed over a period of 0.5–20 days in a batch or fed-batch process at a temperature in the range of between 0 and 45° C. and a pH between 2 and 10. Preferred fermentation conditions are a temperature in the range of between 20 and 37° C. and a pH between 3 and 9. The appropriate conditions are selected based on the choice of the expression host.

After fermentation, the cells are removed from the fermentation broth by means of centrifugation or filtration. After removal of the cells, the enzyme may then be recovered and, if desired, purified and isolated by conventional means.

The product is stably formulated either in liquid or dry form. For certain applications, immobilization of the enzyme on a solid matrix may be preferred.

Enzymes produced by means of the present invention, may be applied either alone, or together with other selected enzymes in a variety of processes requiring the action of an arabinoxylan-degrading enzyme.

The arabinoxylan degrading enzyme of the present invention is used in the treatment or preparation of food (for example, bread), feed and beverages (for example, beer and fruit juices).

The arabinoxylan degrading enzyme is also advantageously used in the preparation and treatment of paper and pulp especially in combination with endoxylanases.

As illustrated in the present invention the arabinoxylan degrading enzyme is added to animal feeds which is rich in arabinoxylans. When added to feeds (including silage) for monogastric animals (e.g. poultry or swine) which contain cereals such as barley, wheat, maize, rye or oats or cereal by-products such as wheat bran or maize bran, the enzyme significantly improves the break-down of plant cell walls which leads to better utilization of the plant nutrients by the animal. As a consequence, growth rate and/or feed conversion are improved. Moreover, arabinoxylans degrading enzymes may be used to the reduce the viscosity of feeds containing arabinoxylans.

An arabinoxylan degrading enzyme may be added beforehand to the feed or silage if pre-soaking or wet diets are preferred. More advantageously, the AXDA produced via the present invention continue to hydrolyse arabinoxylans in the feed in vivo.

Arabinoxylan degrading enzymes are also useful in the preparation of bread as illustrated in Example 8.

Experimental

Strains

*E. coli* BB4 (Silvay et al., 1984): el4 (mcrA) hsdR514, supE44, supF58, lacY1, or Δ(lac1ZY)6, galK2, galT22, metB1, trpR55, Δ(argF-lac)U169 [F', proAB, lacI$^q$ZΔM15, Tn10, (tet$^r$)].

*E. coli* DH5α (Hanahan, 1983): supE44, ΔlacU169, (Φ80lacZΔM15), hsdR17, recA1, endA1, gyrA96, thi-1, relA1.

*E. coli* LE 392 (Murray, 1977): el4 (mcrA) hsdR514, supE44, supF58, lacY1, or Δ(lac1ZY)6, galK2, galT22, metB1, trpR55.

*E. coli* XL1-Blue MRF' (Jerpseth et al., 1992): Δ(mcrA) 183, Δ(mcrCB-hsdSMR-mrr)173, endA1, supE44, thi-1, recA1, gyrA96, relA1, lac, [F', proAB, lacI$^q$ZΔM15, Tn10, (tet$^r$)].

*Aspergillus niger* N400 (CBS 120.49).

*Aspergillus niger* N402 (cspA1) Goosen et al., 1987).

*Aspergillus niger* NW219 (leuA1, nicA1, pyrA6).

Vectors pBluescript SK +/− (Short, J. M., et al., 1988).

pUC19 (Yanish-Perron et al., 1985).

The following solutions were prepared according to Sambrook et al. (1989):

Buffers: TE, 50*TAE, 20*SSC; hybridization, 100* Denhardts, SM DNA loading

Media: NZYCM, LB and minimal medium.

Visniac solution was prepared according to Visniac and Santer (1957).

EXAMPLE 1: Enzyme Isolation

EXAMPLE 1.1 Purification and Characterization of *A. niger* var *tubigensis* Arabinoxylan Degrading Activity A (AXDA)

*A. niger* var *tubigensis* DS 16813 was grown up as described in EPA 0 463 706 without yeast extract and 2% of a crude wheat arabinoxylan fraction instead of oat spelt xylan. The cells were removed by filtration and the supernatant was dried by ultrafiltration.

For the purification of AXDA, 5 grams of the crude enzyme preparation was diluted in 100 ml 10 mM Tris/HCl pH 8.0. The enzyme solution was filtered (Seitz/supro no 250 and Seitz/supro EKS) and diluted to a final protein concentration (Biorad protein assay) of 5.2 g/l. The crude enzyme was fractionated by HPLC (Waters Preparative 650 Advanced Protein Purification System) on a DEAE TSK 650 (M) anion exchange column (600 ml) (rate 25 ml/min). The column was equilibrated with 25 mM Tris/HCl (pH 8.0). The sample (3 g protein) was applied to the column and eluted with a gradient of the equilibration buffer containing 100 mM NaCl. The AXDA enzyme was eluted at a NaCl concentration of 53 mM as shown in FIG. 1.

EXAMPLE 1.2: pH Optimum

For the determination of the pH optimum of the AXDA crude enzyme preparation, the Water Insoluble Solids (WIS) polymer fraction of maize was used as substrate. 1.6 mg of the crude enzyme preparation was added to 0.5 g WIS and diluted to 5 ml with buffer (100 mM NaAc) of pH varying from 3.40 to 7.65. The samples were incubated for 60 minutes at 39° C. and centrifugated for 15 minutes (2800 g). In the supernatant, reducing sugars were measured using Sumner reagent.

Preparation of the Sumner reagent: 10 g phenol is added to 22 mol of 10% NaOH the volume is then adjusted to 100 ml with demineralized water. 10 g of $NaHSO_3$ is added. To 70 ml of this solution 300 ml 4.5% NaOH is added followed by 255 g K/Na tartrate and 800 ml 1% 3,5-dinitrosalicylic acid. The mixture is then stirred at room temperature until the chemicals are dissolved. 0.5 ml of the Sumner reagent is added to 200 ul sample and boiled for 10 minutes. After cooling 5 ml demineralized water is added. The extinction is measured at 515 nm. The reducing sugar content of the samples is calculated using a calibration curve of xylose.

Figure 2:
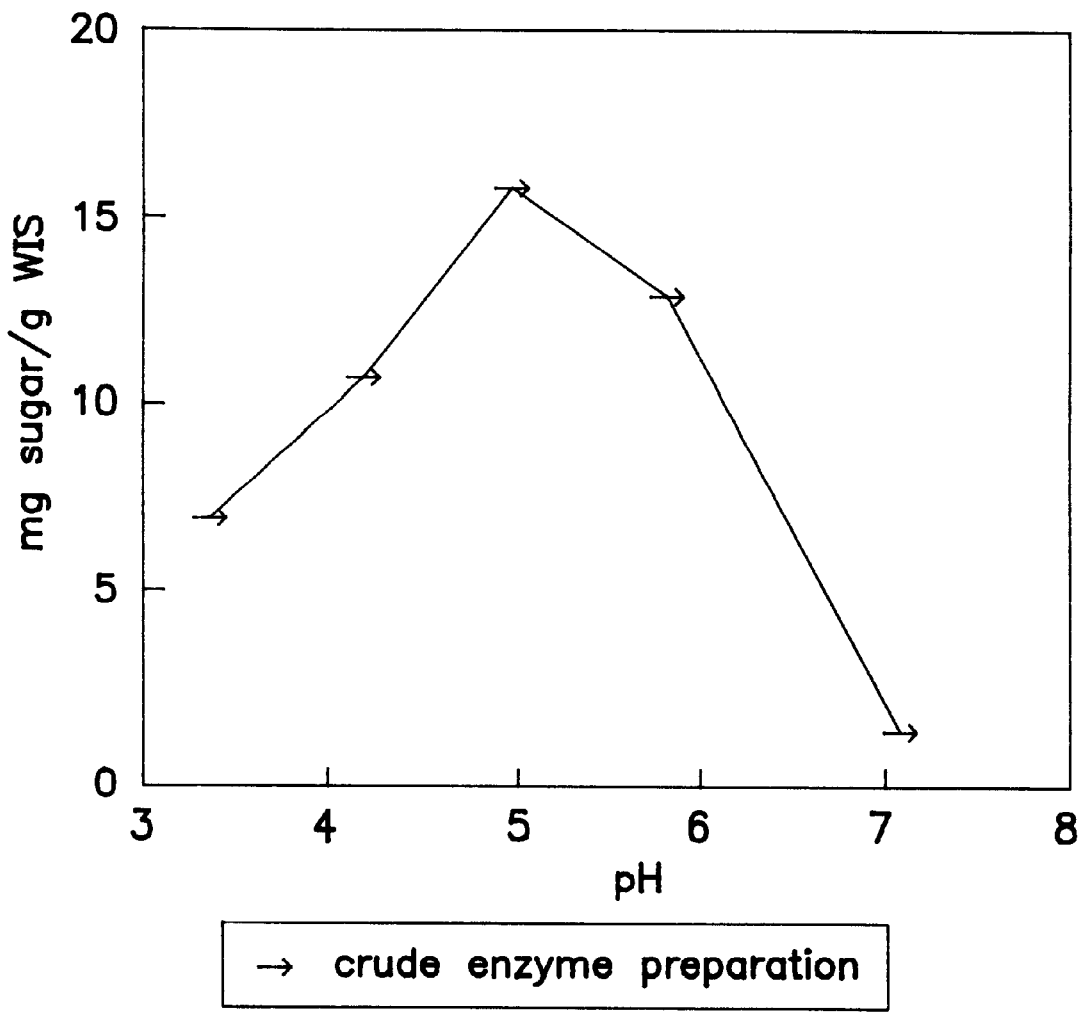
FIG. 2 diagram showing the activity of AXDA on the water insoluble solids (WIS) fraction of maize as a function of pH.

The pH optimum for the enzyme was 5.0. as shown in FIG. 2.

EXAMPLE 1.3: Amino Acid Composition

From the AXDA fractions of the DEAE column the amino acid composition was measured on a PICO-TAG 150 MM column (detection at 254 nm). The following composition was found:

TABLE 1

Amino acid composition of AXDA

| amino acid | mM | calculated mol (%) |
|---|---|---|
| ASP | 1.11 | 13.43 |
| GLU | 0.66 | 8.13 |
| SER | 1.00 | 12.13 |
| GLN | 0.00 | 0.00 |
| GLY | 0.84 | 10.25 |
| HIS | 0.12 | 1.30 |
| ARG/ASN | 0.18 | 2.12 |
| THR | 0.71 | 8.48 |
| ALA | 0.74 | 8.83 |
| PRO | 0.34 | 4.00 |
| TYR | 0.46 | 5.54 |
| VAL | 0.43 | 5.06 |
| MET | 0.11 | 1.30 |
| ILE | 0.29 | 3.42 |
| LEU | 0.S2 | 6.12 |
| PHE | 0.43 | 5.18 |
| LYS | 0.38 | 4.59 |

HPLC pump: CM4000; detection M440, 254 nm; injection 4 ul, Gilson 232; column PICO-TAG 150 MM; data system: Maxima.

EXAMPLE 1.4: Biochemical Characterisation (IEP and Molecular Weight)

The IEP of AXDA was determined on a Pharmacia minigel pH 3–9. The protein was stained with a Pharmacia silver stain solution. The IEP of the AXDA enzyme was estimated to be 3.6.

The molecular weight of AXDA was determined on a Pharmacia mini gradient SDS-gel (10–15%) and the proteins were detected with silver staining (Pharmacia). The molecular weight of AXDA was estimated to be 32 kDa.

EXAMPLE 1.5: Protein Sequencing of *A. niger* var *tubigensis* Arabinoxylan Degrading Activity A (AXDA)

EXAMPLE 1.5.1: Amino Acid Sequencing of the N-terminus of *A. niger* var *tubigensis* Arabinoxylan Activity A (AXDA)

Approximately 1 nmol (~30 µg) AXDA was subjected to electrophoresis on a 15% SDS-polyacrylamide gel, followed by electroblotting onto Immobilon-P membrane (Millipore), according to the method described by Matsudaira (1987). The membrane fragment containing the main band having an apparent molecular weight (SDS-page) of 32 Kda was subjected to sequence analysis in gas-phase sequencing (Amons, 1987) (SON facility, Leiden). The following sequence was determined:

Lys—?—Ala—Leu—Pro—Ser—Ser—Tyr    (SEQIDNO: 1)

EXAMPLE 1.5.2: Amino Acid Sequence Determination of a CNBr Peptide of Arabinoxylan Degrading Activity A (AXDA)

Approximately 2 nmol AXDA was subjected to chemical cleavage by CNBr. Approximately 2 nmol (~60 µg) AXDA was freeze-dried and resuspended in 60 µl 70% formic acid containing 125 µg CNBr (2.5 mg/ml). This reaction mixture was incubated in the dark at room temperature for 48 hours. The liquid was evaporated in a Speedvac, washed with sterile bidest and evaporated again. This wash step was repeated twice. The reaction mixture was then subjected to electrophoresis on a 15% SDS-polyacrylamide gel, followed by electroblotting onto Immobilon-P membrane (Millipore), according to the method described by Matsudaira (1987). The membrane fragment containing the main band having an apparent molecular weight (SDS-page) of approximately 9 kDa was subjected to sequence analysis in gas-phase sequencing (Amons, 1987) (SON facility, Leiden). The following sequence was determined:

CNBr peptide:

Ile—Val—Glu—Ala—Ile—Gly—Ser—Thr—Gly—His—Arg—
Tyr—Phe—(Arg/Asn)—(Ser)—(Phe)—(Thr)    SEQIDNO:2)

Ambiguous amino acids are given between brackets.

EXAMPLE 2: Enzymatic Profile of AXDA

α-Arabinofuranosidase activity was measured on a paranitro phenyl arabinofuranoside substrate (Sigma). To 1 ml substrate, 300 µl enzyme solution was added. After 15 minutes incubation at 30° C. the reaction was stopped with 5 ml $Na_2CO_3$ (5M). The extinction was measured at 402 nm. The α-arabinofuranosidase activity was calculated (volume * extinction)/(E * time). The crude enzyme preparation contained an α-arabinofuranosidase activity of 0.30 pNPAF U/mg. The fractions from the DEAE column were tested for activity. The arabinofuranosidase active pool contained 3.0 pNPAF U/mg (see FIG. 1). Other fractions with α-furanosidase activity were not found. The α-arabinofuranosidase active pool was later tested on a water insoluble polymer fraction of maize and no activity on this substrate was measured.

This indicated that AXDA has no α-arabinofuranosidase activity on paranitrophenyl substrate.

In a further attempt to identify the enzymatic acitivity of AXDA, filtrates of an *Aspergillus niger* culture transformed with the *Aspergillus tubigensis* axdA-gene were screened for activity on a substrate consisting of wheat arabinoxylan. The tubigensis gene was placed under control of the pyruvate kinase (a glycolytic) promoter and the growth conditions were chosen so to favour expression of the transgene, avoiding expression of endogenous arabinose degrading enzymes. Accordingly, it was determined that AXDA had arabinose-releasing activity on high molecular weight arabinoxylan substrates. Protein content was determined using the Sedmak method. Activity of AXDA was determined by adding 100 µl of different dilutions (in 10 mM Na-acetate buffer pH 5.0) of the culture filtrates to 150 μl 50 mM Na-acetate (pH 5.0) and 250 μl 0.4% wheat arabinoxylan (Megazyme), and incubation at 40° C. for one hour. The reaction was stopped by heating the mixtures during 10 minutes at 100° C. Arabinoxylan degradation products were monitored using HPAEC (high performance anion exchange chromatography), using the heat-inactivated incubations as samples.

The results were as follows:

TABLE 0

Activity of *Aspergillus tubigensis* AXDA on wheat arabinoxylan

| Sample | Protein content (mg/100 mg) | Units AXDA/ml | Specific Activity |
|---|---|---|---|
| A 3003#12 (conc) | 0.057 | 22.4 | 191.5 |
| B 3003#15 (conc) | 0.064 | 31.48 | 233.2 |
| C 3003#12 (perm) | * | 0.028 | — |
| D 3003#15 (perm) | * | 0.032 | — |

*One unit of arabinosefuranohydrolase activity is defined as the amount of enzyme capable of releasing 1 μmole arabinose from arabinoxylan per minute.

It was concluded that the AXDA enzyme of *Aspergillus tubigensis* has arabinofuranohydrolase (AXH) activity.

Arabinase activity was measured with an arabinase test kit from Megazyme, and executed following the instructions. In the experiment, the AXDA pool of the DEAE column showed no activity on linear arabinan.

This indicated that AXDA is not an arabinase.

Endoxylanase activity was measured on oats spelt xylan. 10 ml 5% xylan suspension (100 mM NaAc pH 3.5) was boiled for 10 minutes. After cooling down, the suspension was incubated at 39° C. for 10 minutes. The reaction was started by adding 0.5 ml enzyme solution. After several periods of incubation (5, 10, 15, 20, and 25 minutes), 1.5 ml sample, from the 39° C. incubation, was added to 1.5 ml demineralized water and boiled for 10 minutes. The samples were centrifuged for 15 minutes (2800 g). On the supernatant, reducing sugars were detected with the Sumner reagent (see Example 1.2).

In the AXDA fraction pool an endoxylanase activity of 399.0 U/mg was found. Endoxylanase and AXDA were later tested in an in vitro digestion system (see Example 6).

From that it was concluded that the endoxylanase activity in the AXDA fraction pool was an activity associated with a different polypeptide activity. A further indication that a polypeptide having endo-xylanase co-elutes with an enzyme similar to AXDA, is found by Kormelink (1992, PhD. Thesis, Chapter 6, p. 107, last two paragraphs and page 108). It is concluded that AXDA has no endo-xylanase activity of itself.

EXAMPLE 3: Construction of the cDNA Expression Library

EXAMPLE 3.1: Induction and Isolation of mRNA

An *A. niger* N400 culture was grown for 69 and 81 h respectively, as described in EPA 0 463 706 without yeast extract and 2% of a crude wheat arabinoxylan fraction instead of oat spelt xylan, after which mycelium was harvested by filtration and then washed with sterile saline. The mycelium was subsequently frozen in liquid nitrogen after which it was powdered using a Microdismembrator (Braun). Total RNA was isolated from mycelial powder in accordance with the guanidium thiocyanate/CsCl protocol described in Sambrook et al. (1989), except that the RNA was centrifuged twice using a CsCl gradient. Poly A⁻ mRNA was isolated from 5 mg of total RNA by oligo(dT)-cellulose chromatography (Aviv and Leder, 1972, Sambrook et al., 1989) with the following modifications: SDS is omitted from all solutions and the loading buffer was supplemented with 9% (v/v) dimethylsulfoxide.

EXAMPLE 3.2: Construction of the cDNA Library cDNA was synthesized from 7 μg poly A⁺ mRNA and ligated into bacteriophage lambdaλ Uni-ZAP XR using the ZAP™-cDNA synthesis kit (Stratagene) according to the manufacturers instructions. After ligation of the cDNA into Uni-ZAP XR vector-arms, the phage DNA was packaged using Packagene™ extracs (Promega) according to the manufactures instructions. Ligation of 120 ng cDNA in 1.2 μg vector arms and subsequent packaging of the reaction mixture resulted in a primary library consisting of 3.5 * 10⁴ recombinant phages. This primary library was amplified using *E. coli* XL1-Blue MRF', titrated and stored at 4° C.

EXAMPLE 4: Screening of the *A. niger* N400 cDNA Library for the (axdA) with Antibodies Raised Against AXDA and Isolation of cDNA Clones EXAMPLE 4.1: Preparation of Antibodies Raised Against AXDA in a Rabbit 500 μg of AXDA was dialized against 1 mM phosphate buffer pH 7.0 and freeze-dried. The protein was resuspended in 1 ml sterile PBS (0.136 M NaCl; 2.7 mM KCl; 8 mM $Na_2HPO_4$; 1.75 mM $KH_2PO_4$; pH 7.4). To this protein mixture, 1 ml of Freunds' complete adjuvants was added and vortexed for 30 minutes to obtain a stabile emulsion. This mixture was injected into the rabbit subcutaneously. In week 6 a booster was given by injecting 250 μg AXDA in 0.5 ml sterile PBS to which 0.5 ml of Freunds+ incomplete adjuvants was added. The rabbit was bleeded in week 7 and the serum tested. In week 13 the rabbit was given a second booster of 250 ∞g followed by a bleeding in week 14. This procedure of boosters with an interval of 6 weeks followed by a bleeding may be repeated several times.

The collected blood was incubated for 30 at 37° C. and subsequently stored at 4° C. for 16 hours. After centrifugation at 5000 rpm in a Sorvall High speed centrifuge the serum was collected.

EXAMPLE 4.2: Immunoscreening of the *A. niger* N400 cDNA Library with Antibodies Raised Against $AXDA_{TUB}$ To screen the *A. niger* N400 cDNA library, constructed as described in Example 3.2, for axdA cDNA clones 5 * 10³ pfu per plate were plated in NZYCM topagarose containing 0.7% agarose on 85-mm-diameter NZYCM (1.5% agar) plates as described (Maniatis et al., 1982, pp. 64), using *E. coli* BB4 as plating bacteria.

Two replicas of each plate were made on nitrocellulose filters (Schleicher and Schüll BA85) as described by Sambrook et al. (1989, pp. 12.16–12.17). $AXDA_{NIG}$ was visualized using antibodies raised against purified $AXDA_{TUB}$ (Example 4.1) after immunostaining as described in European Patent Application 91205944.5 (publication no. 0 463 706 A1). Immunostained plaques, appearing in duplicate on the replica filters, were identified; 8 positive plaques were selected. Each positive plaque was lifted from the plate using a Pasteur pipette and the phages were eluted from the agar plug in 1 ml of SM buffer containing 20 μl chloroform, as described in Maniatis et al. (1982, pp. 64). The phages obtained were purified by repeating the procedure described above using filter replicas from plates containing 50–100 plaques of the isolated phages.

After purification the phages were propagated by plating $5 \times 10^3$ phages on NZYCM medium. After overnight incubation at 37° C. confluent plates were obtained, from which the phages were eluted by adding 5 ml SM buffer and storing the plate for 2 h. at 4° C. with intermittent shaking. After collection of the supernatant using a pipette, the bacteria were removed from the solution be centrifugation at 4,000 x g for 10 min. at 4° C. To the supernatant 0.3% chloroform was added and the number of pfu was determined. These phage stocks contain approximately $10^{10}$ pfu/ml.

EXAMPLE 4.3: Restriction Analysis on axdA cDNA Clones

The recombinant Uni-ZAP XR clones containing axdA cDNA were converted to Bluescript phagemids using super-infection with the filamentous helper phage ExAssist™, which is included in the ZAP™-cDNA synthesis kit from Stratagene, according to the manufacturers instructions.

The phagemid DNA was subsequently isolated as described in Sambrook et al. (1989, pp. 1.25–1.28).

The isolated DNA of the 8 axdA cDNA clones were subjected to restriction analysis using the following restriction enzymes: EcoRI and XhoI. The DNA digested for 2 hours at 37° C. in a reaction mixture composed of the following solutions; 2 µl ($\approx 1$ µg) DNA solution; 2 µl of the appropriate 10*React buffer (BRL); 10 U of each Restriction enzyme (BRL) and sterile distilled water to give a final volume of 20 µl. After addition of 4 µl DNA loading buffer the samples were loaded on a 0.7% TAE-agarose gel. The DNA fragments were separated by electrophoresis at 80 V for 1.5 hours.

The restriction analysis revealed that the axdA CNDA clones had a molecular size of approximately 1.2 kb.

EXAMPLE 4.4
Sequence analysis on *A. niger* axdA cDNA clones

The primary structure of the cDNA clones was determined by sequence analysis combined with the use of specific oligonucleotides as primers in the sequencing reactions.

The nucleotide sequences were determined by the dideoxynucleotide chain-termination procedure (Sanger et al., 1977) using the Pharmacia T7 DNA polymerase sequencing kit. Computer analysis was done using the PC/GENE program.

EXAMPLE 4.5
$^{32}$P-labelling of fragment

The *A. niger* axdA cDNA clone fragment was isolated and labelled as descried in European Patent application 91205944.5 (publication no. 0 463 706 A1, Examples 2.2 and 7.1, incorporated herein by reference).

EXAMPLE 4.6
Screening of the *A. niger* var *niger* genomic library for axdA gene and isolation of the gene For the screening of the *A. niger* var *niger* genomic library, constructed as described by Harmsen et al. (1990), for the axdA gene $3 \times 10^3$ pfu per plate were plated in NZYCM top-agarose containing 0.7% agarose on five 85-mm-diameter NZYCM (1.5% agar) plates as described (Maniatis et al., 1982, pp. 64), using *E. coli* LE392 as plating bacteria.

After overnight incubation of the plates at 37° C. two replicas of each plate were made on HybondN filters (Amersham) as described in Maniatis et al. (1982, pp. 320–321).

After wetting the filters in 3×SSC the filters were washed for 60 min. at room temperature in 3×SSC. The filters were prehybridized at 65° C. for two hours in prehybridization buffer containing; 6×SSC, 0.5% SDS, 10×Denhardt's solution, 0.01 M EDTA and 100 µg/ml heat denatured herring sperm DNA (Boerhinger Mannheim). After two hours prehybridization the prehybridization buffer was replaced by hybridization buffer which was identical to the prehybridization buffer, but contains $^{32}$-P labelled 1.2 kb fragment containing *A. niger* axdA cDNA clone (see Example 4.3) and prepared as described in Example 4.5. The filters were hybridized for 18 h at an temperature of 65° C.

After hybridization the filters were first washed at 65° C. for 30 minutes in 5*SSC/0.1% SDS followed by a second wash at 65° C. during 30 minutes in 2*SSC/0.1% SDS. The filters were then washed at 65° C. for 30 minutes with 0.1*SSC/0.1% SDS, followed by a last wash at 65° C. for 30 minutes in 0.1*SSC. The air dried filters are taped on a sheet of Whatman 3MM paper, keying marks were made with radioactive ink and the Whatman paper and filters were covered with Saran Wrap. Hybridizing plaques were identified by exposure of Kodak XAR X-ray film for 72 h at –70° C. using an intensifying screen.

Ten positive hybridizing plaques, appearing in duplicate on the replica filters were found. Four positive plaque were lifted from the plate using a Pasteur pipette and the phages were eluted from the agar plug in 1 ml of SM buffer containing 20 µl chloroform, as described in Maniatis et al. (1982, pp. 64). The phages obtained were purified by repeating the procedure described above using filter replicas from plates containing 50–100 plaques of the isolated phages.

After purification the phages were propagated by plating $5 \times 10^3$ phages on NZYCM medium. After overnight incubation at 37° C. confluent plates were obtained, from which the phages were eluted by adding 5 ml SM buffer and storing the plate for 2 h. at 4° C. with intermittent shaking. After collection of the supernatant using a pipette, the bacteria were removed from the solution by centrifugation at 4,000×g for 10 min. at 4° C. To the supernatant 0.3% chloroform was added and the number of pfu is determined. These phage stocks contain approximately $10^7$ pfu/ml.

EXAMPLE 4.7
Isolation of DNA from bacteriophage lambda

Each of the isolated phages were propagated by combining $5*10^9$ *E. coli* LE392 bacteria in 300 µl SM buffer with $2*10^6$ pages and incubation at 37° C. for 15 min. After the incubation period the infected bacteria were used to inoculate 100 ml prewarmed (37° C.) NZYCM medium and was subsequently incubated for 9–12 hrs at 37° C. in a New Brunswick rotation shaker at 250 rpm, after which period the bacteria were lysed. The bacterial debris was removed by centrifugation for 10 min. at 10.000 rpm. at 40° C., in a Sorvall High speed centrifuge. The phages were precipitated from the supernatant obtained (100 ml) by the addition of 10 g polyethyleneglycol-6000 and 11.7 g NaCl and storing the solution overnight at 4° C. The precipitated phages were collected by centrifugation at 14,000×g at 4° C. for 20 min. The supernatant was removed by aspiration, while the last traces of liquid were removed using a paper towel. The phages were carefully resuspended in 4 ml SM buffer and extracted once with an equal volume chloroform.

Before the DNA was extracted from the phage particles, DNA and RNA originating from the lysed bacteria was removed by incubation of the phage suspension with DNase I and RNase A (both 100 µg/ml) for 30 min. at 37° C. The phage DNA was subsequently released from the phages by the addition of EDTA to a final concentration of 20 mM while the protein was removed from the solution by extracting twice with an equal volume phenol/chloroform/isoamyl alcohol (25:24:1). After separation of the phases by centrifugation using a Sorvall centrifuge (14,000×g, 10 min.), the aqueous phase was extracted once with an equal volume chloroform/isoamylalcohol (24:1). The phases were separated by centrifugation after which the DNA was precipitated from the aqueous phase by the addition 0.1 vol. 5 M sodiumperchlorate and 0.1 vol. isopropanol and incubation on ice for 30 min. The DNA was recovered by centrifugation for 10 min. at 4° C. (14,000×g). The supernatant was removed by aspiration after which the DNA was resuspended in 400 µl TE buffer. The DNA was precipitated once again from this solution by the addition of 0.1 vol. 3 M sodium acetate and 2 vol. ethanol. The DNA was collected by centrifugation for 10 min. at 4° C. (14,000×g). The supernatant was removed by aspiration, the remaining pellet was briefly dried under vacuum, after which the DNA was resuspended in 125 µl TE buffer containing 0.1 µg/ml RNase A. This purification procedure results in the isolation of approximately 50–100 µg DNA from each phage.

EXAMPLE 4.8

Southern analysis of *A. niger* var *niger* axdA DNA containing phages

The isolated DNA of phages $\lambda_{nigaxd1}$ to $\lambda_{nigaxd4}$ was analyzed by Southern analysis using the following restriction enzymes; KpnI, SalI; SstI; XbaI and XhoI for the combination KpnI+XbaI; KpnI+SstI and KpnI+XhoI for 5 hours at 37° C. in a reaction mixture composed of the following solutions; 5 µl (≈1 µg) DNA solution; 2 µl of the approximate 10×React buffer (BRL); 10 U Restriction enzyme (BRL) and sterile distilled water to give a final volume of 20 µl. After digestion the DNA was precipitated by the addition of 0.1 vol. 3 M NaAc and 2 vol. ethanol. The DNA was collected by centrifugation for 10 min. at room temperature (14,000×g). The supernatant was removed by aspiration, the remaining pellet was briefly dried under vacuum and resuspended in sterile distilled water. After addition of 4 µl DNA loading buffer the samples were incubated for 10 min. at 65° C. and rapidly cooled on ice, before loading the samples on a 0.6% agarose gel in TAE buffer. The DNA fragments were separated by electrophoresis at 25 V for 15–18 h.

After electrophoresis the DNA as transferred and denatured by alkaline vacuum blotting (VacuGene XL, Pharmacia LKB) to nylon membrane (HybondN, Amersham) as described in the instruction manual (pp. 25–26) and subsequently prehybridized and hybridized using the labelled *A. niger* axdA cDNA clone as described in Example 4.6 and the hybridization conditions as described in Example 3.3. The hybridization pattern is obtained by exposure of Kodak XAR-5 X-ray film for 18 h. at −70° C. using an intensifying screen.

From the results obtained it was concluded that eh DNA of all four isolated clones hybridized with *A. niger* axdA cDNA. In all four clones fragments originating from the same genomic region were found.

EXAMPLE 4.9

Subcloning of the *A. niger* var *niger* axdA gene

The 3.7 kb XhoI fragment from $\lambda_{nigaxd1}$ was isolated from 0.7% agarose gel by the freeze-squeeze method: After electrophoresis the appropriate band is sliced out and gently shaken for 30 minutes in 1 ml FS1 solution (0.3 M NaAc pH 7.0; 1 mM EDTA). The agarose slice was transferred to a 0.5 ml eppendorf tube, which contained a small silicanized glass wool plug and a hole in the bottom, and frozen in liquid nitrogen. The 0.5 ml tube was then transferred to a 1.5 ml eppendorf tube and subsequently centrifuged for 10 minutes. To the supernatant ⅕₀ volume of FS2 solution (0.5 M $MgCl_2$5; 5% acetic acid) was added and 2.5 volumes 100% ethanol. After 20 minutes incubation at −70° C., the DNA was collected by centrifugation for 15 minutes at 14,000*g at 4° C. After removal of the supernatant, the DNA pellet was dried using a Savant Speedvac vacuum centrifuge. The DNA is dissolved in 10 µl TE buffer and the concentration is determined by agarose electrophoresis, using lambda DNA with a known concentration as a reference and ethidiumbromide staining to detect the DNA.

The vector Pbluescript SK⁻ digested with XhoI and dephosphorylated with alkaline phosphatase prepared as follows: 1 µl (1 µg/µl) pBluescript was mixed with 2 µl 10*React 2 (BRL), 1 µl (1U/µl) XhoI and 16 µl sterile distilled water. The DNA was digested for 2 hours at 37° C., after which 0.5 µl alkaline phosphatase (1 U/µl) (Pharmacia) was added, followed by further incubation at 37° C. for an additional 30 minutes. The linearized vector was isolated from a 0.7% agarose gel as described above.

The 3.7 kb XhoI fragment was ligated in the XhoI digested, dephosphorylated pBluescript SK⁻ vector via the following procedure: 40 ng pBluescript fragment was mixed with 300 ng 3.7 kb XhoI fragment and 4 µl 5*ligation buffer (500 mM Tris-HCl, pH 7.6; 100 mM $MgCl_2$; 10 mM ATP; 10 mM dithiothreitol; 25% PEG-6000) and 1 µl (1U/µl) T4 DNA ligase (BRL) was added to this mixture, resulting in a final volume of 20 µl. The resulting plasmid was designated pIM3002. After incubation for 16 h at 16° C. the mixture is diluted to 100 µl with Ca-HEPES pH 7.0 buffer. 10 µl of the diluted mixture is used to transfer *E. coli* DH5α competent cells prepared as follows: 200 µl of an *E. coli* DH5α overnight culture pregrown in LB medium (LB medium per 1000 ml: 10 g trypticase peptide (BBL), 5 g yeast extract (BBL), 10 g NaCl, 0.5 mM Tris-HCl pH 7.5). This culture was incubated in an orbital shaker at 37° C. until its density corresponds to an O.D.₆₀₀ of 0.15–0.2. The bacteria were then collected by centrifugation at 5000 rpm at 4° C. After discarding the supernatant the cells were kept on ice constantly. The bacterial pellet was washed in 100 ml 100 mM $MgCl_2$, 5 mM Tris-HCl pH 7.4 by resuspending these cells followed by centrifugation as described above. This was repeated with 100 ml 100 mM $CaCl_2$, 5 mM Tris-HCl pH 7.4. Finally the cells were resuspended in 2 ml 100 mM $CaCl_2$, 5 mM Tris-HCl pH 7.4, 14% glycerol. Aliquots (50 µl) were either used immediately for transformation or frozen at −70° C.

*E. coli* DH5α competent cells were used in transformation experiments by combining 50 µl of the cells suspension with 4.5 µl of the ligation mixture. After a 30 minutes incubation period on ice, the cells were incubated for 2 minutes at 42° C. Then 1 ml LB medium was added and the cells were incubated at 37° for 1 hr. The bacteria were then collected by centrifugation at 14,000 g for 30 s. After discarding the supernatant the cells were resuspended in 200 µl LB medium. The resulting bacterial suspension was plated on LB medium containing 100 µg/ml ampicillin, 50 µg/ml X-gal and 60 µg/ml IPTG.

A selection of twelve of the resulting colonies was grown overnight in LB medium containing 100 µg/ml ampicillin. From the cultures plasmid DNA is isolated by the alkaline lysis method as described by Maniatis et al. (1982, pp.

Figure 4:
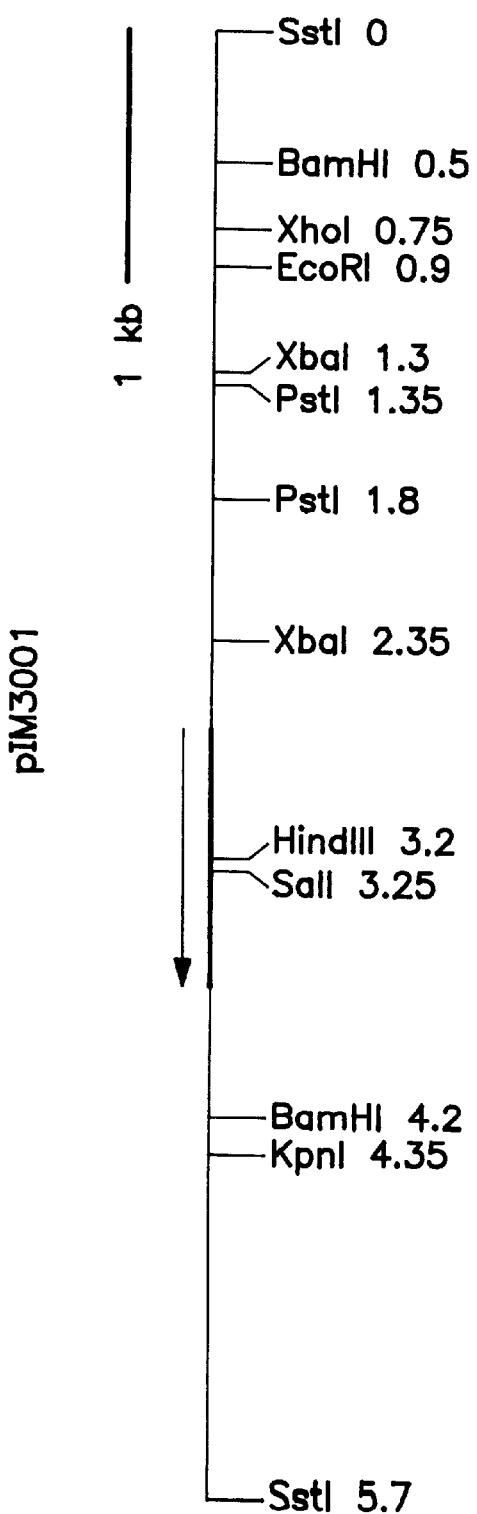
FIG. 4 Map of restriction sites in pIM3001.
Figure 5:
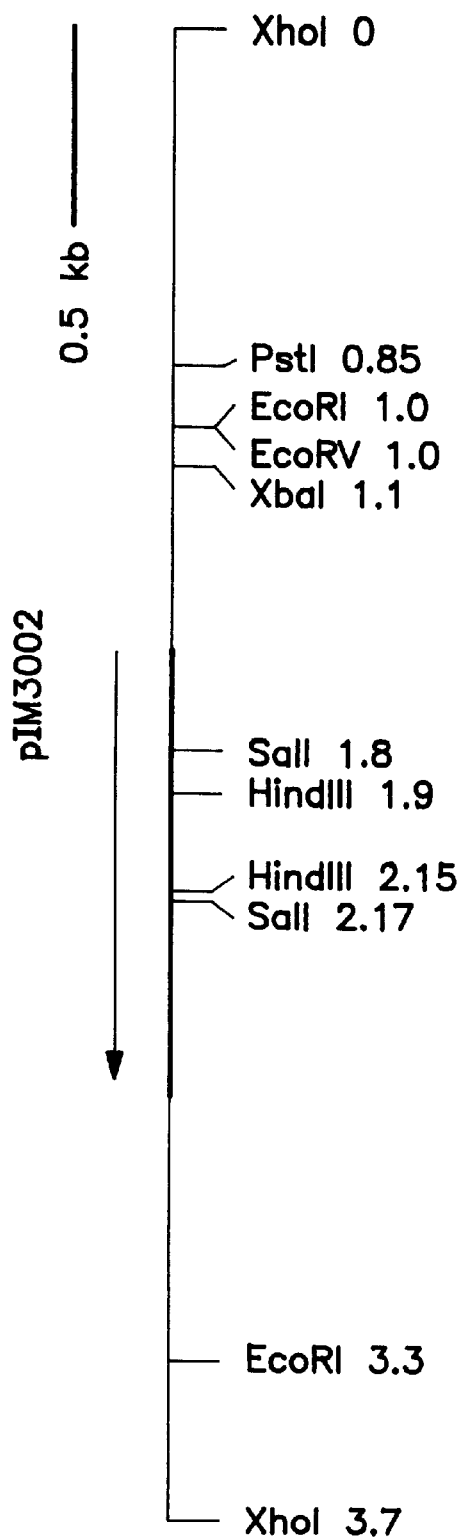
FIG. 5 Map of restriction sites in pIM3002.

368–369), which is used in restriction analysis, as described in Example 4.3 to select a clone harboring the desired plasmid. Plasmid DNA is isolated on a large scale from 250 ml cultures E. coli DH5α containing the plasmid pIM3002 grown in LB medium containing 100 μg/ml ampicillin using the Nucleobond PC-500 kit (Nagel) according to the manufacturer's instructions. The plasmid pIM3002 is further analyzed by restriction enzymes resulting in the restriction map shown in FIG. 4. A sample of E. coli DH5α containing pIM3002 has been deposited on Aug. 28, 1995 at the CBS, Baarn, The Netherlands, under number CBS 637.95.

EXAMPLE 4.10

Overexpression of the cloned gene in A. niger NW219

EXAMPLE 4.10.1

Introduction of the A. niger var niger axdA in A. niger NW219 by cotransformation The plasmid PIM3002, obtained in Example 4.9 was introduced in A. niger by cotransformation of A. niger NW219 using the A. niger pyrA as a selection marker on the plasmid pGW635 (Goosen et al., 1987) and the plasmid PIM3002 as the cotransforming plasmid. A sample of A. niger NW219 was deposited on Aug. 25, 1995, at the CBS, Baarn, The Netherlands, under number CBS 635.95.

Protoplasts were prepared from mycelium by growing A. niger NW219 on minimal medium supplemented with 0.5% yeast extract, 0.25% casamino acids, 50 Mm glucose, 10 Mm nicotinamide and 10 Mm uridine for 18 h at 30° C. The preparation of protoplasts of A. niger NW219 and the transformation procedure was performed as described by Goosen et al., 1987. The resulting PYR$^+$ transformants were analyzed for the expression of the A. niger var niger axdA gene by Western blot analysis.

EXAMPLE 4.10.2

Screening of transformants for the expression of the A. niger var niger axdA gene The transformants obtained in Example 4.10.1 were analyzed for the formation of the A. niger var niger axdA gene product, the AXDA$_{NIG}$ protein. Nineteen of these transformants were used in a growth experiment to analyze for AXDA$_{NIG}$ expression. The A. niger N402 strain was used as the wild type control. The transformants were grown, as described in Example 3.1, for 24, 40, 48 and 68 hours. After growth, the mycelium was removed by filtration and the culture filtrate was analyzed by Western blotting using antibodies raised against AXDA$_{TUB}$ in a rabbit (Example 4.1). Eight of the nineteen transformants analyzed overproduced the AXDA$_{NIG}$ protein as detected by this procedure.

EXAMPLE 4.11

Sequence analysis and description of the A. niger var niger axdA gene

The sequence of the A. niger var niger axdA gene, its promoter/regulation region, the structural part of the gene and the termination region, was determined by subcloning fragments from pIM3002 pBluescript SK$^-$ and pUC19 in combination with the use of specific oligonucleotides as primers in the sequencing reactions. The nucleotide sequence was determined as described in Example 4.4 ) (SEQIDNO: 5).

The sequence obtained comprises 2101 bp, 783 bp in the 5' non-coding region and 322 bp in the 3' non-coding region. In the 5' non-coding region a TATA box is found at positions 665–670. The coding part of the A. niger axdA gene is 996 bp long and is not interrupted by introns. The gene encodes a protein 332 amino acids in size. The N-terminal sequence, as determined in Example 1.5.1 based on the A. niger var. tubigensis AXD A protein, is preceded by a 26 amino acids long prepeptide. The mature protein is 306 amino acids in size and has a predicted molecular weight of 33.101 kDa and a theoretical isoelectric point of 4.07.

EXAMPLE 5.1

Cloning of cDNA fragment containing A. niger var. tubigensis axdA sequences obtained by PCR

EXAMPLE 5.1.1

Generation of cDNA fragments by PCR

The partial amino acid sequence of the internal CNBr fragment (SEQIDNO: 2) as it was determined for AXDA$_{TUB}$ was used to a design oligonucleotide mixture. The following mixture was derived, 5'-ATG ATK GTI GAR GCI ATK GG-3'(20-mer) (SEQIDNNO: 3)

in which I stands for an inosine; K for an A, T or C and R for an A or G. This oligonucleotide was derived from the internal amino acid sequence of AXDA$_{TUB}$, as described above in Example 1.4.2 from amino acid 1 (I) to amino acid 6 G. The ATG was derived from the methionine which is known to be present at the N-terminal end of the peptide fragment because of the CNBr-cleavage mechanism.

The oligo nucleotide mixture was used in PCR (Saiki et al., 1988) in combination with the oligonucleotide T7 (Stratagene) 5'AAT ACG ACT CAC TAT AG-3' (17-mer) (SEQIDNO: 4) using cDNA which was isolated as described in Example 4.7.

For a PCR 2 μl of the resulting λ-cDNA was combined with 5 μl 10*reaction buffer (100 mM Tris-HCl, pH 8.3; 500 mM KCl; 15 mM MgCl$_2$; 0.01% gelatin), 4.0 μl 1.25 mM of each of the four deoxynucleotide triphosphates and 0.5 μg of the oligonucleotides in a final volume of 50 μl. The reaction mixture was mixed and 0.5 μl TAQ polymerase (5 U/μl) (HT Biotechnology, Cambridge UK) was added. The DNA was heat denatured by incubation for 3 minutes at 95° C. followed 25 cycli of 1 minutes at 95° C., 1 minutes at 42° C. and 1 minutes at 72° C. After these 25 cycli the mixture was incubated for 5 minutes at 72° C. Analysis of the reaction products revealed two discrete products of about 500 bp and 600 bp. Based on an apparent molecular weight of 32 kDa for AXDA and apparent molecular weight of 9 kDa for the CNBr peptide, the fragment was in the expected limits.

EXAMPLE 5.1.2

Cloning and analysis of the 500 bp and 600 bp PCR fragments

EXAMPLE 5.1.2.1

Cloning of the 500 bp and 600 bp PCR fragments

Both the 500 bp as the 600 bp PCR fragments were ligated into a pGEM™-T (Promega) vector according to the manufactures instructions. After incubation for 16 hours at 14° C., 4.5 μl of the ligation mixture was used to transform E. coli DH5α competent cells. A selection of six of the resulting colonies from each ligation was grown overnight in LB medium containing 100 μg/ml ampicillin. From the cultures plasmid DNA was isolated by the alkaline lysis method as described by Maniatis et al. (1982, pp. 368–369).

EXAMPLE 5.1.2.2

Sequence analysis of the 500 bp and 600 bp PCR fragments

The primary structures of both the 500 bp and the 600 by PCR fragment were determined by sequencing of the fragments as described in Example 4.4.

Computer analysis of the nucleotide sequences of both PCR fragments showed that the 600 bp PCR fragment did not have any similarity with known arabinoxylan degrading genes and is therefore regarded as a PCR artifact. The nucleotide sequence of the 500 bp PCR fragment was very similar to the nucleotide sequence of the cDNA clone shown in FIG. 4 from nucleotide 706 to 1204.

EXAMPLE 5.2
$^{32}$P-labelling of 500 bp PCR fragment

The 500 bp fragment obtained by PCR was isolated and labelled as described in European Patent application 91205944.5 (publication no. 0 463 706 A1, Examples 2.2 and 7.1, incorporated herein by reference).

EXAMPLE 5.3
Screening of the *A. niger* var *tubigensis* genomic library for axdA gene For the screening of the *A. niger* var *tubigensis* genomic library, constructed as described in case European Patent Application 91205944.5 (publication no. 0.463 706 A1), Example 2, for the axdA gene 3×10$^3$ pfu per plate were plated as described in Example 4.6, with $^{32}$P labelled 500 bp PCR fragment, prepared as described in Example 5.1.1, as probe.

Three of the hybridizing plaques, appearing in duplicate on the replica filters, were identified and were designated $\lambda_{tubaxh1}$ to $\lambda_{tubaxh3}$. The phages were isolated and propagated as described in Example 4.6.

EXAMPLE 5.4
Southern analysis of *A. niger* var *tubigensis* axdA DNA containing phages DNA was isolated from lambda bacteriophages as described in Example 4.7. The isolated DNA of phages $\lambda_{tubaxd1}$ to $\lambda_{tubaxd3}$ was analyzed by Southern analysis using the following restriction enzymes; BamHI; EcoRI; HindIII; KpnI; SalI; SstI and XhoI. The Southern analysis was conducted as described in Example 4.8.

From the results obtained it was concluded that the DNA of all three isolated clones hybridized with the *A. niger* var *tubigensis* axdA cDNA. In all three clones fragments originating from the same genomic region were found.

EXAMPLE 5.5
Subcloning of the *A. niger* var *tubigensis* axdA gene

The 5.5 kb SstI fragment from $\lambda_{tubaxd3}$ was isolated and ligated into the vector pBluescript SK$^-$ SstI digested and dephosphorylated as described in Example 4.9, resulting in a plasmid designated as pIM3001. The plasmid pIM3001 is further analyzed by restriction enzymes resulting in the restriction map shown in FIG. 6. A sample of *E. coli* DH5α harboring pIM3001 was deposited on Aug. 28, 1995 at the CBS, Baarn, The Netherlands, under number CBS 636.95.

EXAMPLE 5.6
Expression of the cloned *A. niger* var *tubigensis* axdA gene in *A. niger* NW219

EXAMPLE 5.6.1
Introduction of the *A. niger* var *tubigensis* axdA gene in *A. niger* NW219 by cotransformation The plasmid pIM3001, obtained in Example 5.5 was introduced in *A. niger* by cotransformation of *A. niger* NW219 as described in Example 4.10.1. The resulting PYR$^+$ transformants were then analyzed for the expression of the *A. niger* var *tubigensis* axdA gene by Western blot analysis.

EXAMPLE 5.6.2
Screening of transformants for the expression of the *A. niger* var *tubigensis* axdA gene The transformants obtained in Example 5.6.1 were analyzed for the formation of the *A. niger* var *tubigensis* axdA gene product, the AXDA$_{TUB}$ protein. Nineteen of these transformants were used in a growth experiment to analyze for AXDA$_{TUB}$ expression. The *A. niger* N402 strain was used as a wild type control. The transformants were grown as described in Example 3.1 for 20, 41, 60 and 86 hours. After growth, the mycelium was removed by filtration and the culture filtrate was analyzed by Western blotting using antibodies raised against AXDA$_{TUB}$ in a rabbit (Example 4.1). Twelve of the nineteen transformants analyzed produced the AXDA$_{TUB}$ protein as detected by this procedure.

EXAMPLE 5.7
Sequence analysis and description of the *A. niger* var *tubigensis* axdA gene The sequence of the *A. niger* var *tubigensis* axdA gene, its promoter/regulation region, the structural part of the gene and the termination region, was determined by subcloning fragments from pIM3001 in pBluescript SK$^-$ and pUC19 in combination with the use of specific oligonucleotides as primers in the sequencing reactions. The nucleotide sequence was determined as described in Example 4.4. (See SEQIDNO: 7).

The sequence obtained comprises 2859 bp, 823 bp in the 5' non-coding region and 1041 bp in the 3' non-coding region. In the 5' non-coding region a CAAT box is found at positions 651–655 and TATA box is found at positions 713–720. The coding part of the *A. niger* var. *tubigensis* axdA gene is 996 bp long and is not interrupted by introns. The gene encodes a protein 332 amino acids in size. The N-terminal sequence, as determined in Example 1.5.1, is preceded by a 26 amino acids long prepeptide. The mature protein is 306 amino acids in size and has a predicted molecular weight of 33.250 kDa and a theoretical isoelectric point of 4.20.

EXAMPLE 6
In vitro digestion of maize with AXDA

EXAMPLE 6.1
Isolation of Water Insoluble Solids (WIS)

For the in vitro digestion system the insoluble polymer fraction of maize was isolated. Maize was milled (3 mm) in a Retsch miller and defatted with hexane (soxlet construction for distillation ) for 6 hours. After defatting, the maize was dried at 105° C. and milled again (1 mm, Retsch miller). To 400 g of the defatted maize, 1.5 l, 1.5% SDS/0.05% β-mercapto-ethanol was added and stirred at room temperature for 1 hour (to break down the proteins) after which was centrifugated for 15 minutes at 24,000 g. After denaturation of the protein the pellet was washed 3 times with 1 l SDS/β-mercapto ethanol, and 2 times with 1 l of demineralized water. The pellet was resuspended in 4 l of demineralized water and sieved on 32 μm. The washing procedure and sieving was repeated. The raw WIS fraction pellet (bigger than 32 μm) was dissolved in 1 l maleate buffer (pH 6.5) and incubated at 90° C. for 50 minutes. 2 mg of α-amylase (Maxamyl™ Gist-brocades) was added and incubated for 16 hours at 30° C., after which it was centrifuged for 15 minutes (24,000 g.). The enzymatic digestion was repeated after which the pellet was washed 3 times with demineralized water of 65° C. The pellet (WIS) was freeze dried. The WIS contained 30% xylose, 29% arabinose, 23% glucose and 7% galactose. The glucose was determined not to be starch (Boeringer Mannheim, starch testkit).

EXAMPLE 6.2

Poultry in vitro digestion system

The dry matter content of WIS was determined (95.73%) by determination of the WIS weight before and after drying at 120° C.

In the poultry in vitro digestion system, to 1 g of WIS 200μ NaN3 (Merck) and 1 ml internal standard (sorbitol; 35 mg/ml, Sigma) was added. For the enzymatic crop digestion (with (200 μg protein) or without enzyme), the sample was filled up with buffer (NaAc, pH 5.5) to 15 ml and incubated at 39° C. for 1 hour. For the stomach digestion, 5 ml of pepsine (5.28 g/l, pH 3.0; Merck) was added and incubated for 1.5 hour at 39° C. For the intestine digestion, 2.5 ml of pancreatin/bile salts (16 g/l, 0.1 g/l respectively; Merck) was added and incubated for 1.5 hour at 39° C. The sample was centrifugated for 15 minutes (2800 g). The supernatant was used to measure the monosugars (HPLC, Spectra Physics; HPX-87P column, Biorad) which were released during the enzymatic digestion. The pellet was dried at 120° C. and the weight was determined. The percentage of dry matter was calculated.

Figure 3:
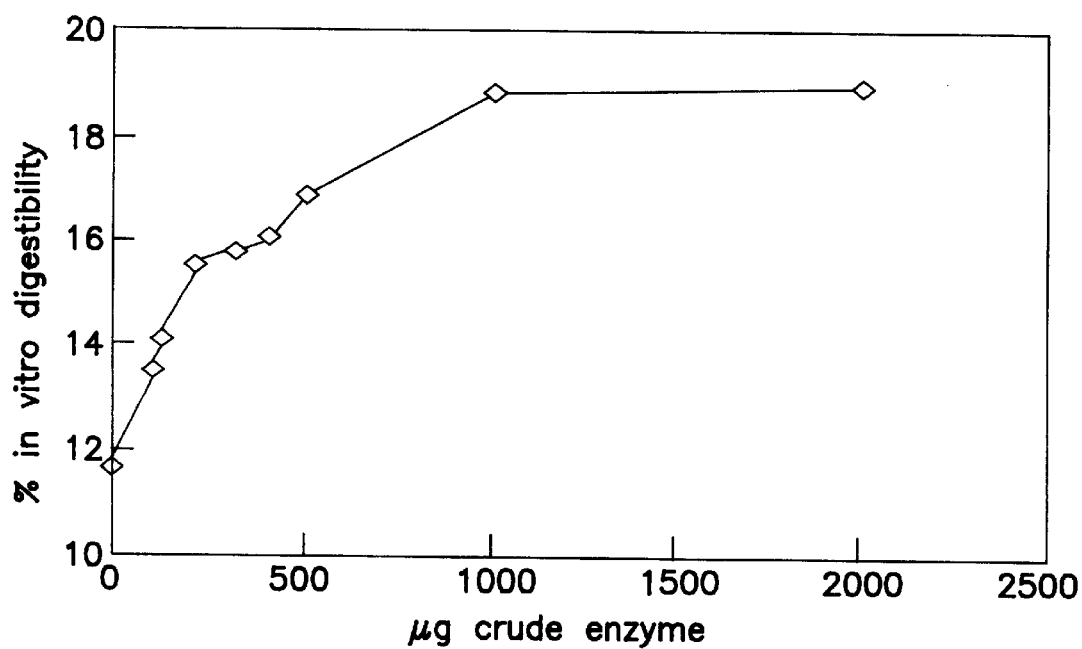
FIG. 3 percentage in vitro digestion of maize WIS as a function of the amount of crude AXDA enzyme.

As a control, in the in vitro system, a dose response of the crude enzyme preparation was added (results are shown in FIG. 3). The AXDA enzyme (200 μg of AXDA protein was added) showed a considerable increase of dry matter digestion as compared to the blanc.

The percentage of dry matter digestion of 15.8% on the maize WIS fraction was an increase of 4.1% to the blanc maize WIS.

EXAMPLE 7

In vitro digestibility experiment with maize WIS

EXAMPLE 7.1

Isolation of maize WIS

The isolation of maize WIS was executed as described in example 6 with some modifications because of the SDS/mercapto ethanol incubation which may not be applied to animal feed. The procedure of isolation was executed on 1 kg of defatted maize. To 1 kg of defatted maize, 4 g papain (Gist-brocades)/100 g maize protein was added and suspended at 30° C. for 2 hours. After this, the suspension was digested with Maxamyl™ (Gist-brocades) 2 ml/l) at 100° C. and centrifugated (15 minutes 24,000 g.). The supernatant was discarded and the enzymatic digestion procedure was repeated on the pellet. The suspension was again centrifugated and washed for 3 times with demineralized water (1 L). After washing, the pellet (water insoluble solids) was freeze dried.

The mono/oligo saccharides content in the maize WIS, was determined by a TriFluorAcetic acid (TFA) analysis. To 0.3 g of WIS, 1 ml 35 mg/ml sorbitol (internal standard), 2 ml demineralized water and 450 μl TFA were added followed by hydrolysis for 1 hour at 120° C. After cooling down, 20 ml of demineralized water was added and hydrolysation was continued for 1 hour at 120° C. After cooling down, the samples were freeze dried and resuspended in 3 ml of demineralized water. The mono saccharides were removed on a HPX-87P column (Biorad) in a HLPC system (Spectra Physics). The WIS polymer fraction of maize contained: 124.8 mg/g xylose; 96.6 mg/g arabinose; 28.2 mg/g galactose and 156.0 mg/g glucose. Because of the high glucose content, the WIS fraction was analyzed for starch (starch test kit, Boehringer Mannheim). The WIS fraction was not found to contain any starch.

EXAMPLE 7.2

Digestibility experiment with broilers

An experiment was performed to detect the influence of enzyme AXDA on the true metabolisable energy content of a diet, to which 20% WIS from maize was added. The method used was a modified "sibbald-assay".

Male broilers (3 weeks of age) were housed individually in cages in an environment-controlled room. Animals were fasted for 48 hours. Then an exactly determined quantity of feed was tube fed. To correct for the loss of endogenous energy containing components, a control-group was included in the experiment. These animals were fed 10 g D-glucose, while the others received 10 g of feed. Each feed was given to 6 animals. The glucose-control group consisted of 5 animals.

Animals were fasted for another 48 hours, during which period the excreta were collected quantitatively. The excreta were stored at −20° C., until analysis was performed. Water was available to the animals during this period once, while they were also once given water by a tube.

The collected digesta were freeze dried and weighed after equilibration to the air. In samples of feed and in samples of the digesta dry matter, nitrogen and energy contents were analyzed.

The results of the control animals were used to correct the results of the animals fed with the experimental diets. The applied method is an adaptation of the experimental procedures described by McNab and Blair, 1988. In that paper a description is given of the methods of analyses and of calculation.

Also in vitro dry matter digestibility measurements were performed, according to the method described in example 6.2.

The experimental treatments were as follows:

I maize basal feed (table 2)

II maize basal feed+10% maize WIS

III maize basal feed+20% maize WIS

IV maize basal feed+20% maize WIS+100 mg/kg AXDA

V maize basal feed+20% maize WIS+45 mg/kg crude enzyme

VI maize basal feed+20% maize WIS+90 mg/kg crude enzyme

VII maize basal feed+20% maize WIS+200 mg/kg endoxylanase.

The composition of the basal diet is given in table 2.

TABLE 2

Composition of a basal diet used in the experiment.

| base feed contents | composition (%) |
|---|---|
| maize | 50.00 |
| tapioca | 19.69 |
| soyflour (50% crude protein) | 19.45 |
| meat and bone meal | 3.60 |
| peas (22.8% cp) | 3.50 |
| fish meal (74% cp) | 1.00 |
| soyoil | 1.00 |
| feather meal (hydrolysed) | 1.00 |
| monocalciumphosphate | 1.23 |
| limestone | 0.90 |
| salt | 0.30 |
| L-lysine.HCl | 0.13 |
| DL-methionine | 0.20 |
| vitamin/mineral premix* | 1.00 |

TABLE 2-continued

Composition of a basal diet used in the experiment.

| base feed contents | composition (%) |
|---|---|

*The vitamin/mineral premix delivered per kg cf feed: riboflavin, 4 mg; niacin, 40 mg; d-pantothenic acid, 12 mg; cholin-chloride, 500 mg; B12, 15 μg; E, 15 mg; K3, 5 mg; retinylacetate, 3.44 mg; cholecalciferol 50 μg; biotin, 0.1 mg; folic acid, 0.75 mg; FeSO4.7H2O, 300 mg; MnO2, 100 mg; CuSO4.5H2O, 100 mg; ZnSO4.7H2O, 150 mg; Na2SeO3, 0.15 mg; antioxidant, 100 mg and virginiamycin, 20 mg.

The results (True Metabolisable Energy corrected for nitrogen (TMEn) and the results of the in vitro assay) are given in table 3.

TABLE 3

True Metabolisable Energy (corrected for nitrogen: TMEn) and in vitro dry matter digestibility.

| treatment | enzyme added | TMEn (KJ/g) | in vitro digestion (%) |
|---|---|---|---|
| I | — | 13.59 a*) | 36.4 |
| II | — | 12.39 b | 36.2 |
| III | — | 11.17 c | 31.9 |
| IV | AXDA | 12.37 | 39.7 |
| V | crude enz. | 11.87 bc | 31.4 |
| VI | crude enz. | 11.63 bc | 33.2 |
| VII | endoxylanase | 11.95 b | 32.6 |

*) Residual standard error: 0.42
LSD (5%): 0.76
TMEn-values with a different letter are significantly (P < 0.05) different according to the LSD-test.

The TMEn-level decreased significantly with an increasing maize-WIS addition.

All enzyme preparations improved TMEn-values, but only for endoxylanase (+7.0%) and for AXDA (+10.7%) this was significant. According to the mean values, AXDA improved the energy value up to the level of the basal feed supplemented with 10% maize-WIS.

In the in vitro model (simulating the digestive process in the chicken), AXDA improved dry matter digestion importantly (+24.5%). Endoxylanase and the crude enzyme preparation were in this model not as effective as AXDA.

EXAMPLE 8

AXDA in bread baking

AXDA was tested in a puploaf baking test using tin breads. Puploaves were baked from 150 g dough pieces obtained by mixing 200 g flour (Robijn™/Columbus™ 80/20), 104 ml water, 1.4 g dried Bakers Yeast (Fermipan™) 4 g salt, 3 g sugar, 400 mg $CaCl_2.2H_2O$, 3 mg (15 ppm) ascorbic acid, and 5 mg (25 ppm) fungal alpha-amylase (Fermizyme™ P200) and 25 ug of purified AXDA. After mixing for 6 min and 15 s at 52 rpm in a pinmixer the dough was divided, proofed for 45 min at 30° C., punched, proofed for another 25 min, moulded and panned. After a final proof of 70 min at 30° C. the dough was baked for 20 min at 225° C. Loaf volume was determined by the rapeseed displacement method. The loaf volume increased from 490 ml (control) to 535 ml for loaves containing AXDA i.e. an increase of 9%.

REFERENCES

Amons, R. (1987), FEBS lett., 212: 68–72.
Carré, B. and Brillouet J. M. (1986), J. Science and Food Agric. 37: 341–351.
Chesson, A. (1987), Recent Advances in Animal Food Nutrition.
Goosen, T. et al. (1987) Curr. Genet. 11: 499–503.
Hanahan, D. (1983) J. Mol. Biol. 166: 557.
Harmsen, J. A. M. et al., (1990) Curr. Genet. 18: 161–166
Haresign, W. and Cole D. J. A., eds. Butterworth, London, 71–89.
Jerpseth, B., et al (1992), Strategies 5: 81–83
Maniatis T., E. F. Fritsch, J. Sambrook (1982): Molecular cloning, a laboratory manual; Cold Spring Harbor Laboratory, New York.
Matsudaira, P. (1987), J. Biol. Chem., 262: 10035–10038.
McCleary, B. V. and Matheson, N. K. (1986), Adv. Carb. Chem. and Biochem. 44: 147–276.
McNab, J. M. and Blair J. C. (1988), British Poultry Science 29: 697–707.
Murray, N. (1977), Mol. Gen. Genet. 150: 53–58
Saiki R. K. et al. (1988), Science, 239, 487–491
Sambrook, J., Fritsch, E. F., Maniatis, T. (1989). In: *Molecular Cloning: a Labatory Manual,* 2nd edn., Cold Spring Harbor Labatory Press, NY.
Sanger, F. Nickelen, S. and Coulson, A. R. (1977), Proc. Natl. Acad. Sci. USA, vol. 74: 5463–5467
Silvay, T. J., Berman, M. L., and Enquist, L. W. (1984) Experiments with gene fusions, Cold Spring Harbor Labatory: New York. pp. xi–xii
Short, J. M. et al., (1988) Nucleic Acids Res. 16: 7583–7600.
Visniac, W. and Santer, M. (1957), Bact. Rev. 21: 195–213
Yanish_perron, C. et al. (1985) Gene 33, 103–119

We claim:

1. A substantially pure polypeptide having arabinoxylan-degrading activity which polypeptide comprises
   a) the amino acid sequence represented by amino acids 1–306 of SEQ ID NO:6;
   b) the amino acid sequence represented by amino acids 1–306 of SEQ ID NO:8;
   c) an amino acid sequence which is a portion of the sequence depicted as amino acids 1–306 of SEQ ID NO:6 or SEQ ID NO:8 wherein said portion retains arabinoxylan-degrading activity;
   d) an amino acid sequence encoded by an allelic variant of SEQ ID NO:5 or SEQ ID NO:7; or
   e) an amino acid sequence encoded by a nucleotide sequence which hybridizes to a DNA fragment as represented by nucleotides 784 to 1779 in SEQ ID NO: 5 or nucleotides 823 to 1818 in SEQ ID NO: 7 or the complements thereof under hybridization conditions which include a first wash at 65° C. for 30 minutes in 5×SSC/0.1% SDS followed by a second wash at 65° C. for 30 minutes in 2×SSC/0.1% SDS followed by a third wash at 65° C. for 30 minutes in 0.1×SSC/0.1% SDS followed by a fourth wash at 65° C. for 30 minutes in 0.1×SSC.

2. The polypeptide in claim 1 which comprises
   a) the amino acid sequence represented by amino acids 1–306 of SEQ ID NO:6;
   b) the amino acid sequence represented by amino acids 1–306 of SEQ ID NO:8;
   c) an amino acid sequence which is a portion of the sequence depicted as amino acids 1–306 of SEQ ID NO:6 or SEQ ID NO:8 wherein said portion retains arabinoxylan-degrading activity; or
   d) an amino acid sequence encoded by an allelic variant of SEQ ID NO:5 or SEQ ID NO:7.

3. The polypeptide of claim 2 which comprises
   a) the amino acid sequence represented by amino acids 1–306 of SEQ ID NO:6;

b) the amino acid sequence represented by amino acids 1–306 of SEQ ID NO:8; or
c) an amino acid sequence which is a portion of the sequence depicted as amino acids 1–306 of SEQ ID NO:6 or SEQ ID NO:8 wherein said portion retains arabinoxylan-degrading activity.

4. The polypeptide of claim 3 which comprises
a) the amino acid sequence represented by amino acids 1–306 of SEQ ID NO:6; or
b) the amino acid sequence represented by amino acids 1–306 of SEQ ID NO:8.

5. A foodstuff which comprises the polypeptide of claim 1.

6. A feed composition which comprises the polypeptide of claim 1.

7. A beverage composition which comprises the polypeptide of claim 1.

8. A pulp processing composition which comprises the polypeptide of claim 1.

9. The polypeptide of claim 1 which is immobilized.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide

```
     (iii) HYPOTHETICAL: NO (iv) ANTI-SENSE: NO (v) FRAGMENT TYPE: N-terminal (vi) ORIGINAL SOURCE:
           (A) ORGANISM: Aspergillus niger var. tubigensis
           (B) STRAIN: DS16813

(xi) SEQUENCE DESCRIPTION: SEQ ID NO:1:

Lys Xaa Ala Leu Pro Ser Ser Tyr
1               5

(2) INFORMATION FOR SEQ ID NO:2:

(i) SEQUENCE CHARACTERISTICS:
           (A) LENGTH: 17 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
           (A) ORGANISM: Aspergillus niger tubigensis
           (B) STRAIN: DS16813

(ix) FEATURE:
           (A) NAME/KEY: Modified-site
           (B) LOCATION: 14
           (D) OTHER INFORMATION: /note= "Arg or Asn"

(xi) SEQUENCE DESCRIPTION: SEQ ID NO:2:

Ile Val Glu Ala Ile Gly Ser Thr Gly His Arg Tyr Phe Xaa Ser Phe
1               5                   10                  15

Thr (2) INFORMATION FOR SEQ ID NO:3:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (vi) ORIGINAL SOURCE:
           (A) ORGANISM: Aspergillus niger var. tubigensis
           (B) STRAIN: DS16813

(ix) FEATURE:
           (A) NAME/KEY: modified_base
           (B) LOCATION: group(9, 15)
           (D) OTHER INFORMATION: /mod_base= i (xi) SEQUENCE DESCRIPTION: SEQ ID NO:3:

ATGATKGTNG ARGCNATKGG                                                    20

(2) INFORMATION FOR SEQ ID NO:4:
```

```
         (i) SEQUENCE CHARACTERISTICS:
              (A) LENGTH: 17 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Aspergillus niger var. tubigensis
              (B) STRAIN: DS16813

(xi) SEQUENCE DESCRIPTION: SEQ ID NO:4:

AATACGACTC ACTATAG                                                   17

(2) INFORMATION FOR SEQ ID NO:5:

(i) SEQUENCE CHARACTERISTICS:
              (A) LENGTH: 2101 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Aspergillus niger
              (B) STRAIN: CBS 120.49

(ix) FEATURE:
              (A) NAME/KEY: TATA_signal
              (B) LOCATION: 665..670

(ix) FEATURE:
              (A) NAME/KEY: CDS
              (B) LOCATION: 784..1779
              (D) OTHER INFORMATION: /product= "arabinoxylan degrading
                   enzyme"
                   /gene= "axdA"
                   /standard_name= "arabinoxylan degrading enzyme"

(ix) FEATURE:
              (A) NAME/KEY: sig_peptide
              (B) LOCATION: 784..861

(ix) FEATURE:
              (A) NAME/KEY: mat_peptide
              (B) LOCATION: 862..1779

(xi) SEQUENCE DESCRIPTION: SEQ ID NO:5:

CTGATTGGGA TTCTGCAGGA ATTCTCTGGG GTATGCCAAA AAAGTATACC GACCTGTAAA      60

AGTCCAACCA GTTCGAAATT ACTAACAATA TGTTTTTGAT CAGGATATCT TTGGCATCTA     120

TGGTGAGAGC CATATCATCA TCTCTTCTTC CGGCAGCTGT CAACTGCCTG CCGAAAGTAC     180

TGGAAGCCAT TGTGTTTTAA GGTGAAACAA GATCAGGGCG GCTATGTGTC AGGGTAGAAC     240

CAGTTTGCTT AGCGCCATCA GGGTCCACGT CTAGACTTTC GATGCCCGGA GTTATTCGCC     300

TTCCCACAGC AGTCATTTCC CCGAATCTAA ACCGATGGAC GGATATTGTG GTGTAATGAT     360

AGAACAACAC GGTGTAGTGT AGTTTTAAGT GCCGTGCTAG ACACGGCAAC GTTCCGGTGG     420

GCGATTGTTT CTGGCTAATG TACTCCGTAG TTTAGGCAAC AGGCCGATCA TCTTCCCCCA     480

TAGGAAAGGA CCCTGAATAG TGCGTCAAAA AGAGCTTGAG GCAAAGGAGG ACTGCACTTT     540
```

-continued

```
CCAAGGCCGA AGTGGGGGGG GGGGATAACC AAGCAGCCCA ACTTTTATCC GAAACCTTTC      600

AGGTGTCATC TAATTTGGAT AAATCCGGAT TGTTCTTCGG CATATGTGGA TGTCACCATG      660

AGCCATAAAT ACAAATATCT GGACAAGCTG TTGCCCTTTG TTCAAGTTAT TCGTTCTCTG      720

TGGACCACGA TCCCAACCAT TGATCTCTTT TGTTTGTTCC TCAGCGGATA AAGTCATACG      780

AAA ATG AAA TTC CTC AAA GCC AAG GGT AGC TTG CTG TCG TCT GGC ATA        828
    Met Lys Phe Leu Lys Ala Lys Gly Ser Leu Leu Ser Ser Gly Ile
    -26 -25             -20                 -15

TAC CTC ATT GCA TTG GCC CCC TTT GTC AAC GCA AAA TGC GCT CTT CCG        876
Tyr Leu Ile Ala Leu Ala Pro Phe Val Asn Ala Lys Cys Ala Leu Pro
    -10             -5                    1                   5

TCG ACA TAT AGT TGG ACT TCG ACC GAT GCT CTC GCC ACC CCA AAG TCC        924
Ser Thr Tyr Ser Trp Thr Ser Thr Asp Ala Leu Ala Thr Pro Lys Ser
                10                  15                  20

GGA TGG ACT GCA CTC AAG GAC TTC ACC GAT GTC GTC TCT AAC GGC AAA        972
Gly Trp Thr Ala Leu Lys Asp Phe Thr Asp Val Val Ser Asn Gly Lys
            25                  30                  35

CAT ATT GTC TAT GCG TCC ACT ACC GAC ACA CAG GGA AAT TAC GGC TCC       1020
His Ile Val Tyr Ala Ser Thr Thr Asp Thr Gln Gly Asn Tyr Gly Ser
        40                  45                  50

ATG GGC TTT GGC GCC TTT TCG GAC TGG TCG GAC ATG GCA TCC GCT AGT       1068
Met Gly Phe Gly Ala Phe Ser Asp Trp Ser Asp Met Ala Ser Ala Ser
    55                  60                  65

CAA ACG GCC ACA AGC TTC AGC GCC GTA GCT CCA ACC TTG TTC TAC TTC       1116
Gln Thr Ala Thr Ser Phe Ser Ala Val Ala Pro Thr Leu Phe Tyr Phe
70                  75                  80                  85

CAG CCA AAG AGT ATC TGG GTT CTG GCC TAC CAA TGG GGC TCC AGC ACT       1164
Gln Pro Lys Ser Ile Trp Val Leu Ala Tyr Gln Trp Gly Ser Ser Thr
                90                  95                  100

TTC ACC TAC CGC ACC TCT CAA GAT CCC ACC AAT GTC AAC GGC TGG TCA       1212
Phe Thr Tyr Arg Thr Ser Gln Asp Pro Thr Asn Val Asn Gly Trp Ser
            105                 110                 115

TCC GAG CAA GCT CTT TTC ACG GGC AAA ATC AGC GGC TCA AGT ACC GGT       1260
Ser Glu Gln Ala Leu Phe Thr Gly Lys Ile Ser Gly Ser Ser Thr Gly
        120                 125                 130

GCC ATT GAT CAG ACT GTG ATT GGT GAT GAT ACG AAT ATG TAT CTT TTC       1308
Ala Ile Asp Gln Thr Val Ile Gly Asp Asp Thr Asn Met Tyr Leu Phe
    135                 140                 145

TTT GCC GGC GAC AAT GGC AAG ATC TAC CGA TCC AGC ATG TCT ATC AAT       1356
Phe Ala Gly Asp Asn Gly Lys Ile Tyr Arg Ser Ser Met Ser Ile Asn
150                 155                 160                 165

GAC TTC CCC GGA AGC TTC GGC AGC CAG TAC GAG GAG ATC CTC AGC GGC       1404
Asp Phe Pro Gly Ser Phe Gly Ser Gln Tyr Glu Glu Ile Leu Ser Gly
                170                 175                 180

GCG ACC AAC GAT TTG TTC GAG GCG GTC CAA GTG TAC ACC GTC GAC GGC       1452
Ala Thr Asn Asp Leu Phe Glu Ala Val Gln Val Tyr Thr Val Asp Gly
            185                 190                 195

GGC GAG GGT GAC AGC AAG TAC CTC ATG ATC GTC GAG GCG ATC GGT TCC       1500
Gly Glu Gly Asp Ser Lys Tyr Leu Met Ile Val Glu Ala Ile Gly Ser
        200                 205                 210

ACC GGA CAT CGT TAT TTC CGC TCC TTC ACG GCC AGC AGT CTC GGC GGA       1548
Thr Gly His Arg Tyr Phe Arg Ser Phe Thr Ala Ser Ser Leu Gly Gly
    215                 220                 225

GAG TGG ACA GCC CAG GCG GCA AGT GAA GAT CAA CCC TTC GCG GGC AAA       1596
Glu Trp Thr Ala Gln Ala Ala Ser Glu Asp Gln Pro Phe Ala Gly Lys
230                 235                 240                 245

GCC AAC AGT GGC GCC ACC TGG ACC GAC GAC ATC AGT CAT GGT GAC TTG       1644
Ala Asn Ser Gly Ala Thr Trp Thr Asp Asp Ile Ser His Gly Asp Leu
                250                 255                 260
```

-continued

```
GTT CGC AAC AAC CCT GAT CAA ACC ATG ACG GTC GAT CCT TGC AAC CTC      1692
Val Arg Asn Asn Pro Asp Gln Thr Met Thr Val Asp Pro Cys Asn Leu
            265                 270                 275

CAG CTT CTC TAC CAG GGC CAT GAC CCC AAC AGC AAT AGT GAC TAC AAC      1740
Gln Leu Leu Tyr Gln Gly His Asp Pro Asn Ser Asn Ser Asp Tyr Asn
            280                 285                 290

CTC TTG CCC TGG AAG CCA GGA GTT CTT ACC TTG AAG CAG TGAAAGGCTT       1789
Leu Leu Pro Trp Lys Pro Gly Val Leu Thr Leu Lys Gln
            295                 300                 305

ATCATTTGGT TGCAGACCGG GGTTTTCTTC CCCTTCCTTG AGTAGTATTG TTGGTGGAAG    1849

ACAGCGGGAT GGGGAGTGAA TACTATCTTG GGCTCAATTG AGGTGGAATC CTGTCAGACT    1909

GTGTACATAG GCTACATGCG AATGATTTGG TTTATTCACA AATAGTATTA ACAGATAGTG    1969

TAGTATACAC CTCTGTATTC ACAGGTGATA GCCTGTCTAC TAGTAGTAGA GATGTGGCTC    2029

GAGATGACTG CACGTGATGA TCACATCATC ATCATCGCAG TCGCTCACGC GACAGTCTCA    2089

GACACACACA TA                                                         2101

(2) INFORMATION FOR SEQ ID NO:6:

(i) SEQUENCE CHARACTERISTICS:
        (A) LENGTH: 332 amino acids
        (B) TYPE: amino acid
        (D) TOPOLOGY: linear (ii) MOLECULE TYPE: protein (xi) SEQUENCE DESCRIPTION: SEQ ID NO:6:

Met Lys Phe Leu Lys Ala Lys Gly Ser Leu Leu Ser Ser Gly Ile Tyr
-26 -25             -20                 -15

Leu Ile Ala Leu Ala Pro Phe Val Asn Ala Lys Cys Ala Leu Pro Ser
-10             -5                   1               5

Thr Tyr Ser Trp Thr Ser Thr Asp Ala Leu Ala Thr Pro Lys Ser Gly
                10                  15                  20

Trp Thr Ala Leu Lys Asp Phe Thr Asp Val Val Ser Asn Gly Lys His
            25                  30                  35

Ile Val Tyr Ala Ser Thr Thr Asp Thr Gln Gly Asn Tyr Gly Ser Met
        40                  45                  50

Gly Phe Gly Ala Phe Ser Asp Trp Ser Asp Met Ala Ser Ala Ser Gln
55                  60                  65                  70

Thr Ala Thr Ser Phe Ser Ala Val Ala Pro Thr Leu Phe Tyr Phe Gln
                75                  80                  85

Pro Lys Ser Ile Trp Val Leu Ala Tyr Gln Trp Gly Ser Ser Thr Phe
            90                  95                  100

Thr Tyr Arg Thr Ser Gln Asp Pro Thr Asn Val Asn Gly Trp Ser Ser
            105                 110                 115

Glu Gln Ala Leu Phe Thr Gly Lys Ile Ser Gly Ser Ser Thr Gly Ala
    120                 125                 130

Ile Asp Gln Thr Val Ile Gly Asp Asp Thr Asn Met Tyr Leu Phe Phe
135                 140                 145                 150

Ala Gly Asp Asn Gly Lys Ile Tyr Arg Ser Ser Met Ser Ile Asn Asp
                155                 160                 165

Phe Pro Gly Ser Phe Gly Ser Gln Tyr Glu Glu Ile Leu Ser Gly Ala
            170                 175                 180

Thr Asn Asp Leu Phe Glu Ala Val Gln Val Tyr Thr Val Asp Gly Gly
            185                 190                 195
```

```
Glu Gly Asp Ser Lys Tyr Leu Met Ile Val Glu Ala Ile Gly Ser Thr
        200                 205                 210
Gly His Arg Tyr Phe Arg Ser Phe Thr Ala Ser Ser Leu Gly Gly Glu
215                 220                 225                 230
Trp Thr Ala Gln Ala Ala Ser Glu Asp Gln Pro Phe Ala Gly Lys Ala
                235                 240                 245
Asn Ser Gly Ala Thr Trp Thr Asp Ile Ser His Gly Asp Leu Val
            250                 255                 260
Arg Asn Asn Pro Asp Gln Thr Met Thr Val Asp Pro Cys Asn Leu Gln
                265                 270                 275
Leu Leu Tyr Gln Gly His Asp Pro Asn Ser Asn Ser Asp Tyr Asn Leu
280                 285                 290
Leu Pro Trp Lys Pro Gly Val Leu Thr Leu Lys Gln
295                 300                 305
```

(2) INFORMATION FOR SEQ ID NO:7:

(i) SEQUENCE CHARACTERISTICS:
        (A) LENGTH: 2859 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Aspergillus niger var. tubigensis
        (B) STRAIN: DS16813

(ix) FEATURE:
        (A) NAME/KEY: CAAT_signal
        (B) LOCATION: 651..655

(ix) FEATURE:
        (A) NAME/KEY: TATA_signal
        (B) LOCATION: 713..720

(ix) FEATURE:
        (A) NAME/KEY: CDS
        (B) LOCATION: 823..1818
        (D) OTHER INFORMATION: /product= "arabinoxylan degrading
            enzyme"
            /gene= "axdA"
            /standard_name= "arabinoxylan degrading enzyme"

(ix) FEATURE:
        (A) NAME/KEY: sig_peptide
        (B) LOCATION: 823..901

(ix) FEATURE:
        (A) NAME/KEY: mat_peptide
        (B) LOCATION: 901..1818

(xi) SEQUENCE DESCRIPTION: SEQ ID NO:7:

```
CATACTGGGT GTGGTACTGT AGGGAACCTG CAGATGCTCT GCCGAAGGTC TGCAAATAGT      60

CCCTGGAGTT TGGTAGTAAA GAGTACCAAC TCGTAAAAGT AGTATGTCCA ACCAATTTGA     120

AAGTACAAAC TTTTAGTTTG ATTGATTAAA ATACTTTTGG TGTGTACAGT GACAGCCAAA     180

ATATCATCTC TTCAGCCGAT AGATGTCAAC TGCCCGCCGA AAGTACCGGA AGGTCGTGGT     240

GTTTTAAGGT GAAACACTAT CAGGGCGGCA ATGTGTCAAA GTAGAACCAG TTTGCTTAGC     300

GCCATTAGGG TCCACGCCTA GACCCCTCGA TGCCCGGGAG TCATCCGTCC TGTCACAGCA     360

ATTATTTCCC CGAGTCTACT GCCGAAGAAG AGCTATTGTG GCGTAATCAT GGAATTACCC     420
```

```
TCTGTGTAGG GTAGTCTTGA ACGCCGTTCT AGACACGGCA ACGTTCCGGT GGACGATCGT    480

TTCTGGCTAA TGTACTCCGT AGTTTAGGCA GCTAGCTGAT CATCTTCCCC CTAGGGAAAG    540

GACCTGAATA GTGCGCCAAA ATGAGCTTGA GCAAAGGAAT GTTCTTTCTA AGCCAAAGTG    600

GGGGAAATAA CCAAGCAGCC CACTTTTATC CGAAACGTTT CTGGTGTCAT CCAATATGGA    660

TAAATCCCGA TTGTTCTTCT GCACGTATCA GTATTGCCAT CAACGTAACT ACATATATTT    720

GAACATGGTC TGGTCCTCCG TTCGATTTAT TCGTTCTCCG TGGCCAACGA CTTCAGCCAT    780

TGATCTCTTT TGTTTCTTTC CTGCGGCTAA ACCCATTCGA AG ATG AAG TTC TTC       834
                                                  Met Lys Phe Phe
                                                  -26 -25
```

```
AAA GCC AAA GGC AGC TTG CTG TCA TCA GGC ATC TAC CTC ATT GCA TTA      882
Lys Ala Lys Gly Ser Leu Leu Ser Ser Gly Ile Tyr Leu Ile Ala Leu
        -20             -15                 -10

ACC CCC TTT GTC AAC GCC AAA TGT GCT CTT CCG TCG TCC TAT AGT TGG      930
Thr Pro Phe Val Asn Ala Lys Cys Ala Leu Pro Ser Ser Tyr Ser Trp
        -5              1               5                   10

AGT TCA ACC GAT GCT CTC GCA ACT CCA AAG TCA GGA TGG ACC GCA CTG      978
Ser Ser Thr Asp Ala Leu Ala Thr Pro Lys Ser Gly Trp Thr Ala Leu
                15                  20                  25

AAG GAC TTT ACT GAT GTT GTC TCG GAC GGC AAA CAT ATT GTC TAT GCG     1026
Lys Asp Phe Thr Asp Val Val Ser Asp Gly Lys His Ile Val Tyr Ala
            30                  35                  40

TCC ACT ACT GAT GAA GCG GGA AAC TAT GGC TCG ATG ACC TTT GGC GCC     1074
Ser Thr Thr Asp Glu Ala Gly Asn Tyr Gly Ser Met Thr Phe Gly Ala
            45                  50                  55

TTC TCA GAG TGG TCG AAC ATG GCA TCC GCT AGC CAG ACA GCC ACC CCC     1122
Phe Ser Glu Trp Ser Asn Met Ala Ser Ala Ser Gln Thr Ala Thr Pro
        60                  65                  70

TTC AAT GCC GTG GCT CCT ACC CTG TTC TAC TTC AAG CCG AAA AGT ATC     1170
Phe Asn Ala Val Ala Pro Thr Leu Phe Tyr Phe Lys Pro Lys Ser Ile
75                  80                  85                  90

TGG GTT CTG GCC TAC CAA TGG GGC TCC AGC ACA TTC ACC TAC CGC ACC     1218
Trp Val Leu Ala Tyr Gln Trp Gly Ser Ser Thr Phe Thr Tyr Arg Thr
                95                  100                 105

TCC CAA GAT CCC ACC AAT GTC AAT GGC TGG TCG TCG GAG CAG GCG CTT     1266
Ser Gln Asp Pro Thr Asn Val Asn Gly Trp Ser Ser Glu Gln Ala Leu
                110                 115                 120

TTC ACC GGC AAA ATC AGC GAC TCA AGC ACC AAT GCC ATT GAC CAG ACG     1314
Phe Thr Gly Lys Ile Ser Asp Ser Ser Thr Asn Ala Ile Asp Gln Thr
            125                 130                 135

GTG ATT GGC GAT GAT ACG AAT ATG TAT CTC TTC TTC GCC GGC GAC AAC     1362
Val Ile Gly Asp Asp Thr Asn Met Tyr Leu Phe Phe Ala Gly Asp Asn
    140                 145                 150

GGC AAG ATC TAC CGA TCC AGC ATG TCC ATC AAT GAC TTC CCC GGA AGC     1410
Gly Lys Ile Tyr Arg Ser Ser Met Ser Ile Asn Asp Phe Pro Gly Ser
155             160                 165                 170

TTC GGC AGC CAG TAC GAG GTG ATC CTG AGT GGC GCC CGC AAC GAT CTA     1458
Phe Gly Ser Gln Tyr Glu Val Ile Leu Ser Gly Ala Arg Asn Asp Leu
                175                 180                 185

TTC GAG GCG GTC CAA GTA TAC ACC GTC GAC GGC GGT GAG GGC GAC ACG     1506
Phe Glu Ala Val Gln Val Tyr Thr Val Asp Gly Gly Glu Gly Asp Thr
            190                 195                 200

AAG TAT CTC ATG ATC GTT GAG GCG ATC GGG TCC ACC GGA CAT CGT TAT     1554
Lys Tyr Leu Met Ile Val Glu Ala Ile Gly Ser Thr Gly His Arg Tyr
        205                 210                 215

TTC CGC TCC TTC ACG GCC AGC AGT CTG GGT GGA GAG TGG ACA GCC CAG     1602
Phe Arg Ser Phe Thr Ala Ser Ser Leu Gly Gly Glu Trp Thr Ala Gln
```

-continued

```
            220                 225                 230
GCG GCA AGT GAG GAT CAA CCC TTC GCA GGC AAA GCC AAC AGT GGT GCC    1650
Ala Ala Ser Glu Asp Gln Pro Phe Ala Gly Lys Ala Asn Ser Gly Ala
235                 240                 245                 250

ACC TGG ACC GAA GAC ATT AGC CAT GGT GAC TTG GTT CGC AAC AAC CCT    1698
Thr Trp Thr Glu Asp Ile Ser His Gly Asp Leu Val Arg Asn Asn Pro
                    255                 260                 265

GAT CAA ACG ATG ACT GTC GAT CCT TGC AAC CTC CAG TTG CTC TAT CAG    1746
Asp Gln Thr Met Thr Val Asp Pro Cys Asn Leu Gln Leu Leu Tyr Gln
                270                 275                 280

GGC CAT GAC CCC AAC AGC AGT GGC GAC TAC AAC CTC TTG CCG TGG AAG    1794
Gly His Asp Pro Asn Ser Ser Gly Asp Tyr Asn Leu Leu Pro Trp Lys
            285                 290                 295

CCG GGC GTC CTT ACC TTG AAG CAG TGAAGGTATT ATAATTAGTT GCAGATTGTG   1848
Pro Gly Val Leu Thr Leu Lys Gln
300                 305

TTTTCATTCC TTCTTCAAGA GTGCTTAGTG GTGGAAGACA GCAGAAGGTG GTCACTATCT  1908

TAGGCTCAGT TGGGGTGGGC TTGTGTCCAT AGGCTAGTAA TGTGCGCATA ATTCAGTTCA  1968

TTGGCAAGGA GTGCGGTATA AATACCTGTT CTCACAAAAA AAAATAGGCC CGGTGGTCAT  2028

ACTCCGTATT GGGATAGAGA TCTCGTAGTA GTAGGATTGT GGGCCTCAGA GGATGACCGA  2088

CACGTGAGCA GTCTCCTTCT ACGGCTAGTC GCGTTCTACA TAAGAAATAG TCAGCTCAGA  2148

GTTTGTTTTT TGGCTACTTT GAAGGATGGC CTATCGAATC GCACGTCTCC TCAATTGGCC  2208

AGGTATTGGC ATTCACTCTC CGCGCTTTGC GGGTGCCGGC ACGAGATGTC TCCTGGAGAA  2268

ACTGGGCAAC GAGCAGACTA CGGATATGGG AGATTGTTGA CGACGTTCTT CTTGGTAAAT  2328

TTGAACCCTT CAGGGGCTCT ATAAAGGCGG AAATCTAAAT CTCATGTGCC CTAACGTGTC  2388

CGACCACGGT GTTGATCAGC ACCTATTAGA TCAGACAACA ACCTTTGGCT CGGAAATTGA  2448

ACAGGTAGCT CTTGAATGAC ACTCTGGATC CTGATTCAAT TTATAATGCG TCACTTGAGC  2508

GTGCAAGGGG TGCTATATTC ACATCTTGCC CCAATCCAAG GGGCGTCGGA TCCCATTGTG  2568

CTCGACAGCC TGGAACTTCG CCGACAGTAT TCTTACGACG TCGATACTGA ATAGTCCAC   2628

CTGGTGTGCA TTCGTACGCC GGAAAGACCC TCGTCCGACC GCGTGGCCTT GATTCTGACG  2688

AGATGCTTCA ACAAGCGGCC AATTCGATGC CAGCTGTTCA TCGGTTAGAT GTGCTACACA  2748

GTGACCTGAT TCCAGGAAAC ATATTCTGGA ACGAAGGAAA TGGCCGCGTC AATTTTCATT  2808

GACTTTGAGT GTGCAATAAC CCAAAATAAC GAAATAATGA ACGACCGCTG T           2859
```

(2) INFORMATION FOR SEQ ID NO:8:

(i) SEQUENCE CHARACTERISTICS:
        (A) LENGTH: 332 amino acids
        (B) TYPE: amino acid
        (D) TOPOLOGY: linear (ii) MOLECULE TYPE: protein (xi) SEQUENCE DESCRIPTION: SEQ ID NO:8:

```
Met Lys Phe Phe Lys Ala Lys Gly Ser Leu Leu Ser Ser Gly Ile Tyr
-26 -25                 -20                 -15

Leu Ile Ala Leu Thr Pro Phe Val Asn Ala Lys Cys Ala Leu Pro Ser
-10                 -5                  1                   5

Ser Tyr Ser Trp Ser Ser Thr Asp Ala Leu Ala Thr Pro Lys Ser Gly
                10                  15                  20

Trp Thr Ala Leu Lys Asp Phe Thr Asp Val Val Ser Asp Gly Lys His
            25                  30                  35
```

-continued

```
Ile Val Tyr Ala Ser Thr Thr Asp Glu Ala Gly Asn Tyr Gly Ser Met
     40                  45                  50

Thr Phe Gly Ala Phe Ser Glu Trp Ser Asn Met Ala Ser Ala Ser Gln
 55                  60                  65                  70

Thr Ala Thr Pro Phe Asn Ala Val Ala Pro Thr Leu Phe Tyr Phe Lys
                 75                  80                  85

Pro Lys Ser Ile Trp Val Leu Ala Tyr Gln Trp Gly Ser Ser Thr Phe
                 90                  95                 100

Thr Tyr Arg Thr Ser Gln Asp Pro Thr Asn Val Asn Gly Trp Ser Ser
            105                 110                 115

Glu Gln Ala Leu Phe Thr Gly Lys Ile Ser Asp Ser Ser Thr Asn Ala
            120                 125                 130

Ile Asp Gln Thr Val Ile Gly Asp Asp Thr Asn Met Tyr Leu Phe Phe
135                 140                 145                 150

Ala Gly Asp Asn Gly Lys Ile Tyr Arg Ser Ser Met Ser Ile Asn Asp
                155                 160                 165

Phe Pro Gly Ser Phe Gly Ser Gln Tyr Glu Val Ile Leu Ser Gly Ala
            170                 175                 180

Arg Asn Asp Leu Phe Glu Ala Val Gln Val Tyr Thr Val Asp Gly Gly
            185                 190                 195

Glu Gly Asp Thr Lys Tyr Leu Met Ile Val Glu Ala Ile Gly Ser Thr
200                 205                 210

Gly His Arg Tyr Phe Arg Ser Phe Thr Ala Ser Ser Leu Gly Gly Glu
215                 220                 225                 230

Trp Thr Ala Gln Ala Ala Ser Glu Asp Gln Pro Phe Ala Gly Lys Ala
                235                 240                 245

Asn Ser Gly Ala Thr Trp Thr Glu Asp Ile Ser His Gly Asp Leu Val
            250                 255                 260

Arg Asn Asn Pro Asp Gln Thr Met Thr Val Asp Pro Cys Asn Leu Gln
            265                 270                 275

Leu Leu Tyr Gln Gly His Asp Pro Asn Ser Ser Gly Asp Tyr Asn Leu
    280                 285                 290

Leu Pro Trp Lys Pro Gly Val Leu Thr Leu Lys Gln
295                 300                 305
```